US011504673B2

(12) United States Patent
Peterson et al.

(10) Patent No.: US 11,504,673 B2
(45) Date of Patent: Nov. 22, 2022

(54) LAYERED MIXED-MATRIX MEMBRANES AND MIXED-MATRIX COMPOSITES FROM POLYMERS AND ACTIVE MATERIALS

(71) Applicants: University of Delaware, Newark, DE (US); Government of the United States, as Represented by the Defense Threat Reduction Agency, Fort Belvoir, VA (US); Government of the United States, as Represented by the Secretary of the Army, Aberdeen Proving Ground, MD (US)

(72) Inventors: Gregory W. Peterson, Bel Air, MD (US); Annie Lu, Washington, DC (US); Thomas H. Epps, III, Bear, DE (US); Jean S. Epps, Bear, DE (US)

(73) Assignees: GOVERNMENT OF THE UNITED STATES, AS REPRESENTED BY THE DEFENSE THREAT REDUCTION AGENCY, Fort Belvoir, VA (US); GOVERNMENT OF THE UNITED STATES, AS REPRESENTED BY THE SECRETARY OF THE ARMY, Aberdeen Proving Ground, MD (US); UNIVERSITY OF DELAWARE, Newark, DE (US)

( * ) Notice: Subject to any disclaimer, the term of this patent is extended or adjusted under 35 U.S.C. 154(b) by 288 days.

(21) Appl. No.: 16/638,817

(22) PCT Filed: Aug. 15, 2018

(86) PCT No.: PCT/US2018/000203
§ 371 (c)(1),
(2) Date: Feb. 13, 2020

(87) PCT Pub. No.: WO2019/194783
PCT Pub. Date: Oct. 10, 2019

(65) Prior Publication Data

US 2021/0129086 A1 May 6, 2021

Related U.S. Application Data

(60) Provisional application No. 62/545,559, filed on Aug. 15, 2017.

(51) Int. Cl.
*B01D 69/12* (2006.01)
*B01D 53/22* (2006.01)
(Continued)

(52) U.S. Cl.
CPC .......... *B01D 69/12* (2013.01); *B01D 53/228* (2013.01); *B01D 67/0079* (2013.01);
(Continued)

(58) Field of Classification Search
None
See application file for complete search history.

(56) References Cited

U.S. PATENT DOCUMENTS 9,694,344 B2 7/2017 Song et al.
2005/0113517 A1* 5/2005 Tayano .................. B32B 27/08 525/196
(Continued)

OTHER PUBLICATIONS

International Preliminary Report on Patentability for International Application No. PCT/US2018/000203, dated Feb. 18, 2020, 6 pages.
(Continued)

*Primary Examiner* — Jason M Greene
(74) *Attorney, Agent, or Firm* — RatnerPrestia

(57) ABSTRACT

Disclosed herein are multi-layer structures comprising a first composite layer disposed over a second composite layer, wherein the first composite layer contains a first active material dispersed in a first polymer containing an elasto-
(Continued)

meric polymer and the second composite layer contains a second polymer which may have a second active material dispersed therein, wherein the first active material chemically or physically interacts with at least one toxic chemical and is selected from the group consisting of metal-organic frameworks (MOFs), metal oxides, metal hydroxides, zeolites, and combinations thereof, and wherein the active material and the second active material (if present) are the same as or different from each other, and the first polymer and second polymer are the same as or different from each other, subject to the proviso that the first composite layer and the second composite layer compositionally differ from each other in at least one respect.

29 Claims, 14 Drawing Sheets

(51) Int. Cl.

| | |
|---|---|
| ***B01D 67/00*** | (2006.01) |
| ***B01D 69/14*** | (2006.01) |
| ***B01D 71/02*** | (2006.01) |
| ***B01D 71/80*** | (2006.01) |
| ***B32B 7/12*** | (2006.01) |
| ***B32B 27/08*** | (2006.01) |
| ***B32B 27/18*** | (2006.01) |
| ***B32B 27/30*** | (2006.01) |

(52) U.S. Cl.

CPC ......... *B01D 69/148* (2013.01); *B01D 71/022* (2013.01); *B01D 71/80* (2013.01); *B32B 7/12* (2013.01); *B32B 27/08* (2013.01); *B32B 27/18* (2013.01); *B32B 27/302* (2013.01); *B01D 2325/20* (2013.01); *B01D 2325/40* (2013.01)

(56) References Cited

U.S. PATENT DOCUMENTS

| | | | | |
|---|---|---|---|---|
| 2010/0260657 | A1* | 10/2010 | Niitsuma | B01D 53/226<br>423/437.1 |
| 2016/0243525 | A1* | 8/2016 | Song | B01J 20/226 |
| 2017/0189866 | A1* | 7/2017 | Koros | B01D 69/148 |
| 2019/0250135 | A1* | 8/2019 | Andersson | B01D 53/228 |

OTHER PUBLICATIONS

International Search Report and Written Opinion for International Application PCT/US2018/000203, dated Nov. 1, 2019, 8 pages.

Wang et al., "Significance of the double layer capacitor effect in polar rubbery dielectrics and exceptionally stable low-voltage high transconductance organic transistors," Scientific Reports, vol. 5, No. 1, Dec. 14, 2015, p. 17849, 8 pages.

Zhou et al., Electrical breakdown and ultrahigh energy density in poly(vinylidene fluoride-hexafluoropropylene) copolymer, Applied Physics Letters, 94, 162901, 2009, 3 pages.

Toxnet. "Soybean Oil." Toxnet—Toxicology Data Network, National Institutes of Health, Apr. 7, 2015, 3 pages.

Lu et al., "MOFabric: Electorspun Nanofiber Mats from PVDF/UiO-66-$NH_2$ for Chemical Protection and Decontamination", Applied Materials & Interfaces, 2017, vol. 9, pp. 13632-13636.

* cited by examiner

LAYERED MIXED-MATRIX MEMBRANES AND MIXED-MATRIX COMPOSITES FROM POLYMERS AND ACTIVE MATERIALS

CROSS-REFERENCE TO RELATED APPLICATIONS

This application is a national stage application under 35 U.S.C. § 371 of International Application No. PCT/US2018/000203, filed Aug. 15, 2018, which claims priority to U.S. Provisional Patent Application No. 62/545,559, filed Aug. 15, 2017, the disclosures of each of these applications being incorporated herein by reference in their entireties for all purposes.

STATEMENT REGARDING FEDERALLY SPONSORED RESEARCH

This invention was made with government support under Grant No. CB3934 awarded by the Joint Science and Technology Office for Chemical Biological Defense (JSTO CBD) and Grant No. PE 0601101A 91 awarded by the United States Army for funding through ECBC's Individual Laboratory Independent Research program. The government has certain rights in the invention.

BACKGROUND OF THE INVENTION

Over the past decade, metal-organic frameworks (MOFs) have become a leading class of porous materials for applications in separations, air purification, catalysis, and sensing. The ability to tune the functionality and pore structure of MOFs allows for unprecedented control at the nanoscale, which has translated to exciting new properties at the macroscale. The development of successful MOF-based technologies not only depends on scaling-related issues, but also the ability to incorporate these highly active assemblies into industry-relevant engineered constructs such as granules and membranes.

Mixed-matrix membranes (MMMs) have previously been prepared using zeolites, metal oxides, and carbons as active fillers for applications in filtration and separations. MMMs also have been fabricated containing MOFs and have demonstrated unique reactive capabilities. However, MMMs have been limited to low MOF mass loadings (less than 20 weight % or 10 weight %), as higher loadings (such as above 30 weight % or above 50 weight % or above 70 weight %) result in catastrophic defects and brittleness. Furthermore, MMMs containing MOFs have been limited to single component systems and therefore lack versatility and multifunctionality. The combination of tailorable MOFs with tunable polymers, and especially block copolymers, enables the optimization of composite materials for specific applications. Traditional MMMs are generally fabricated using one of two techniques: (1) a filler particle (e.g., carbon, zeolite, MOF, etc.) is mixed with a polymer and cast as a freestanding film, or (2) a polymer or inorganic phase is used to grow the MOF as a secondary layer (i.e., templated growth). The former method permits the use of a broad range of MOFs and polymer substrates, as well as provides the ability to scale up MOFs before membrane formation. The latter allows less versatility for the type of MOF used, but generally results in more conformal membranes. Most recent MMM research incorporating MOFs has focused on carbon dioxide (or other gas) separations and sequestration with potential applicability to other areas. To date, one application that has not been actively investigated using MMMs and similar composites is the reactive removal of chemical warfare agents (CWAs).

Recently, Cohen and coworkers utilized the underlying concept of MMMs to produce composites with significantly higher MOF loadings than traditional examples. These mixed matrix composites (MMCs) incorporated MOFs into single-layer freestanding films based on poly(vinylidene fluoride) (PVDF), as well as styrene/butadiene (SBS, SBR) copolymers. In these cases, the main thrust was to investigate a new form factor for MOFs with a focus on high mass loadings. While the strategy was able to incorporate MOFs, the composites generally became fragile at appreciable MOF loadings.

Ideally, films should be developed that can accommodate high MOF loadings while maintaining structural stability. Hence, flexible layered mixed-matrix membranes and composites in the form of multi-layer structures and methods for preparing thereof are provided herein to overcome the above limitations.

SUMMARY OF THE INVENTION

In an aspect, a multi-layer structure is provided, the multi-layer structure comprising a first composite layer disposed over a second composite layer, wherein the first composite layer comprises 1-99% by weight of a first active material dispersed in a first polymer comprising an elastomeric polymer and the second composite layer comprises 0-99% by weight of a second active material dispersed in a second polymer, wherein the first active material is chemically or physically reactive to at least one toxic chemical and is selected from the group consisting of metal-organic frameworks (MOFs), metal oxides, metal hydroxides, zeolites and combinations thereof, and wherein the first active material and the second active material are the same as or different from each other, and the first polymer and second polymer are the same as or different from each other, subject to the proviso that the first composite layer and the second composite layer compositionally differ from each other in at least one respect.

In an embodiment, the elastomeric polymer is selected from the group consisting of elastomeric homopolymers, elastomeric block copolymers, elastomeric random copolymers, elastomeric graft copolymers, elastomeric brush copolymers, and elastomeric thermosets. In another embodiment, the elastomeric polymer is an elastomeric block copolymer selected from the group consisting of styrene-based block copolymers, methyl methacrylate-based block copolymers, and olefin-based block copolymers.

The multi-layer structures of the present disclosure provides many advantages including ability to have higher loadings (such as above 30 weight % or above 50 weight % or above 70 weight %) of active materials in at least one composite layer while maintaining structural integrity, such as flexibility. Furthermore, the multi-layer structures of the present disclosure provide breathable structures, which allows transport of moisture vapor through at least one of the one or more composite layers, while being effective as a barrier to toxic chemicals.

In an aspect, the multi-layer structures of the present disclosure are used as a barrier layer against one or more toxic chemicals in an article selected from the group consisting of gloves, boots, clothing, gas masks, tents, filters, and sensors, wherein the one or more toxic chemicals comprise one or more of ammonia, chlorine, nitrogen dioxide, sulfur dioxide, carbon monoxide, chemical warfare agents, simulants, oils, contaminants, battlefield contaminants and combinations thereof.

In another aspect, a process of making the multi-layer structures of the present invention is provided, comprising the step of mixing an active material with a polymer, optionally in an organic solvent, to form a coating composition and forming at least one of the composite layers by depositing the coating composition using one or more of drawn-down coating (doctor blading), spin-coating, dip-coating, spraying, extrusion, casting, and electrospinning. The process can further include repeating the above steps to form an n-layered multi-layer structure and optionally forming an adhesive polymeric layer in between and in contact with two composite layers.

In another aspect, a method for removing one or more toxic chemicals is provided, comprising the steps of providing a multi-layer structure as disclosed hereinabove, having an outer surface and an inner surface and contacting a feed stream comprising one or more toxic chemicals with the outer surface of the multi-layer structure to produce a toxic chemical-rich retentate stream and a permeate stream, such that the concentration of one or more toxic chemicals in the permeate stream is less than that present in the retentate stream.

In yet another aspect, a method for decontaminating a surface contaminated with one or more toxic chemicals is provided. The method comprising the steps of contacting a multi-layer structure film according to the present disclosure, with a contaminated surface and removing the multi-layer structure film from the contaminated surface, thereby resulting in a decontaminated surface. In such embodiment, the decontaminated surface contains a lower amount of one or more toxic chemicals as compared to the contaminated surface.

In another aspect, a method for sensing one or more toxic chemicals is provided, comprising the steps of providing a multi-layer structure according to the present disclosure, having an outer surface and an inner surface and contacting a feed stream comprising one or more toxic chemicals with the outer surface of the multi-layer structure to produce a toxic chemical-rich retentate stream and a permeate stream. The method further comprises a step of sensing the one or more toxic chemicals in the feed stream by one or more of colorimetric changes, spectral changes, electrical impedance changes, resistive changes, and the like.

In another aspect, a method for separating gases is provided, comprising the steps of providing a first multi-layer structure according to the present disclosure, having an outer surface and an inner surface and contacting a feed stream comprising a mixture of gas A, gas B, and gas C, with the outer surface of the first multi-layer structure to produce a gases A&B-rich retentate gas stream and a gas C-rich permeate gas stream. The method can further include contacting the gases A&B-rich retentate gas stream with the outer surface of a second multi-layer structure of the present disclosure to produce a gas A-rich retentate gas stream and a gas B-rich permeate gas stream.

BRIEF DESCRIPTION OF THE DRAWINGS

The accompanying drawings, which are incorporated in and constitute a part of this specification, illustrate one (several) embodiment(s) of the invention, and together with the written description, serve to explain certain principles of the invention.

DETAILED DESCRIPTION OF THE INVENTION

As used herein the term "multi-layer structure" refers to n-layer structures such as two-layer structures, three-layer structures, etc. The term "multi-layer structure" is used interchangeably with "multi-layer mixed-matrix composite" (MMC), "multi-layer mixed-matrix membrane" (MMM), "composite laminate", "layered composite", and "MOF Sandwich" or "MOFwich", which is a special case where at least one active material is an MOF.

As used herein, the term "active material" refers to any suitable material that can chemically or physically interact with at least one toxic chemical. The interaction could be a chemical reaction or adsorption, for example. Physical interaction includes physical adsorption of the toxic chemical on or by the active material and chemical interaction is meant to include reaction with the active material resulting in decomposition or formation of a new chemical compound.

As used herein, the term "toxic chemical" refers to gaseous, liquid or solid matter that can be hazardous to living organisms. Exemplary toxic chemicals include, but are not limited to, ammonia, chlorine, nitrogen dioxide, sulfur dioxide, carbon monoxide, chemical warfare agents, simulants, oils, contaminants, battlefield contaminants and combinations thereof. Examples of chemical warfare agents include, but are not limited to, mustard gas (HD), Sarin (GB), soman (GD), and VX. Exemplary simulants include, but are not limited to, 2-chloroethyl ethylsulfide (2-CEES), which is a simulant for mustard, dimethyl methylphosphonate (DMMP) and diisopropyl fluorophosphates (DIFP), which are nerve agent simulants. Exemplary oils include, but are not limited to, crude oil, kerosene, gasoline, and the like. Exemplary contaminants include, but are not limited to, $SO_2$, $NO_2$, $CO_2$, and the like. Exemplary battlefield contaminants include, but are not limited to, Jet Propellant 4 (JP4) fuel, Jet Propellant 8 (JP8) fuel, diesel fuel, kerosene, and other hydrocarbons.

Figure 1A:
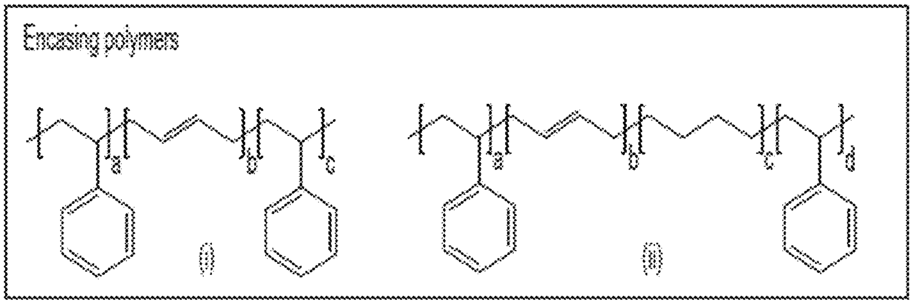
FIGS. 1A and 1B shows exemplary styrene-based block copolymers, which are rubbery (elastomeric) polymers and other polymers which can be brittle, respectively, which can be used in combination with high loading of active materials.
Figure 1B:
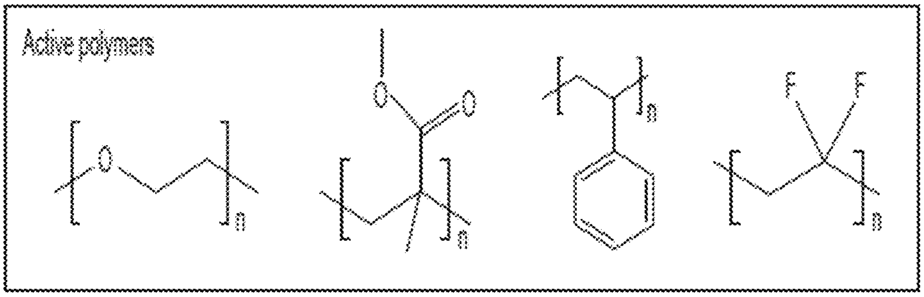
Figure 1C:
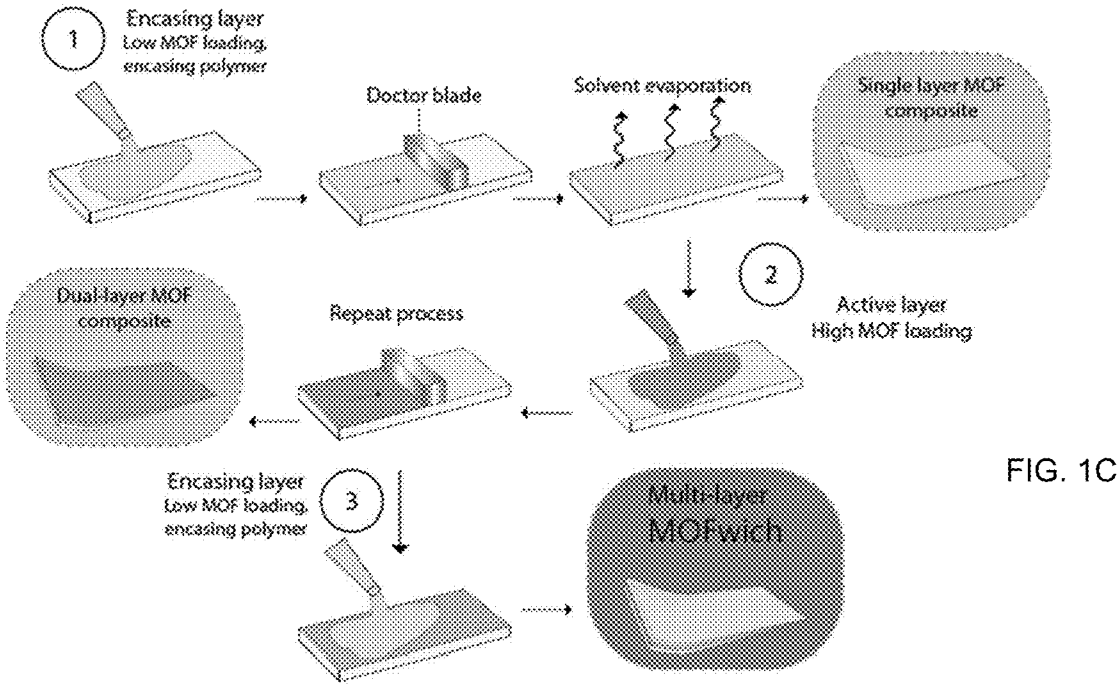
FIG. 1C schematically illustrates a strategy for fabricating a multi-layer structure in accordance with various embodiments of the present invention.
Figure 1D:
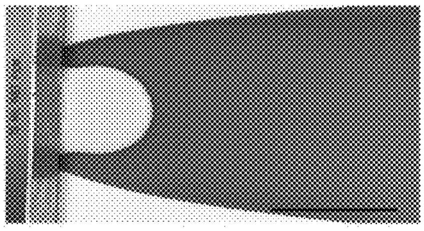
FIG. 1D shows an encasing layer is drawn over a middle layer.
Figure 2:
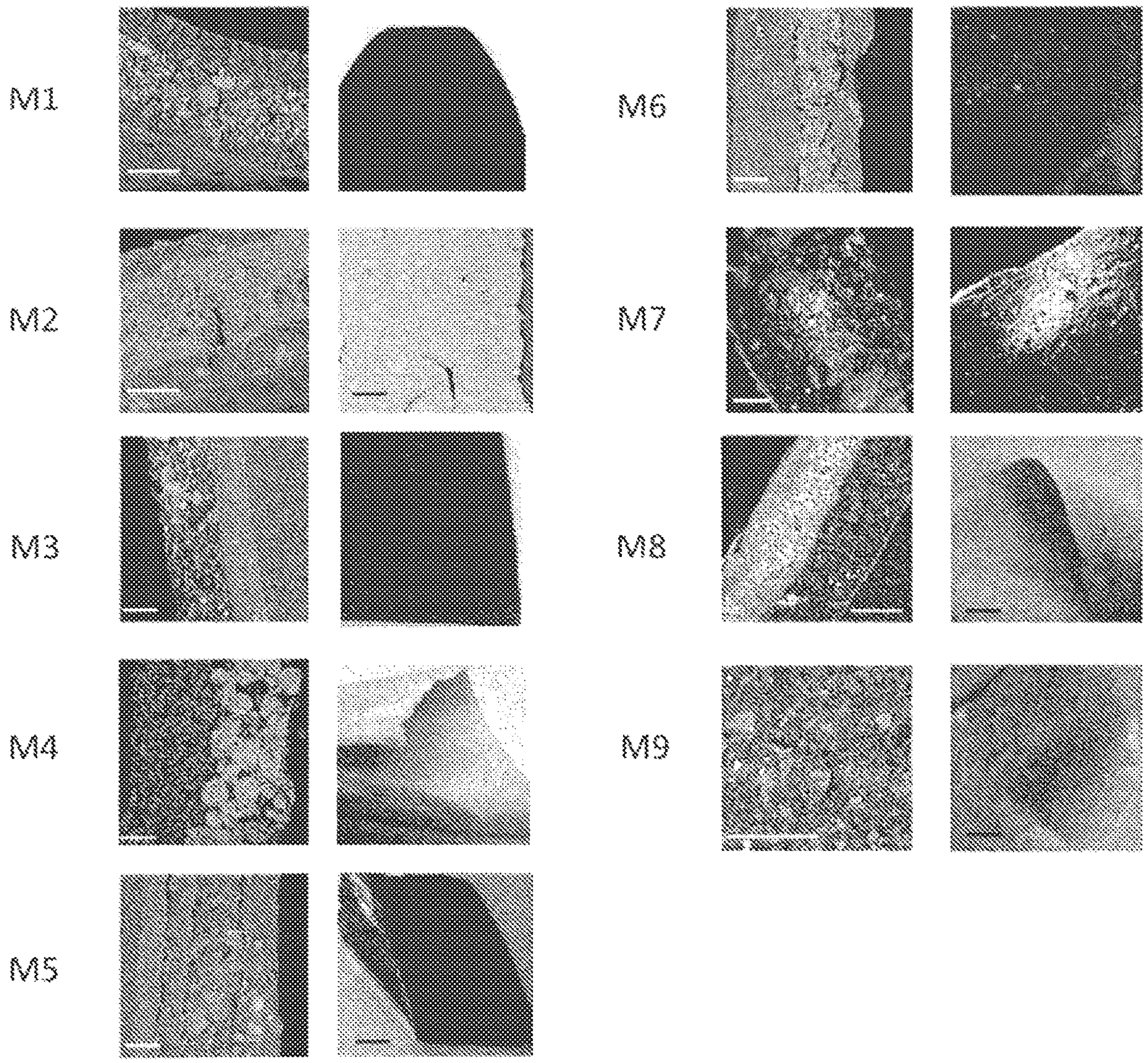
FIG. 2 shows scanning electron micrographs [SEM] (left) and optical microscopy images (right) for each of the two- and three-layer structures (M1-M9), according to various embodiments of the present invention. Scale bar for scanning electron microscopy images=50 μm. Scale bar for optical images=1 cm.

The present invention describes a process and resulting multi-layer structures comprising composite layers of polymer and active material. Specifically, a multi-layer structure may be made from a polymer and a metal organic framework (MOF) mixture using a "draw-down" method, as depicted in FIG. 1C. Once formed, another layer of the same or another polymer/active material mixture is drawn-down on top of the original, and so on. The method allows for a wide range of layered polymer/MOF composites in terms of type of polymer, type of MOF, and weight percentages of each component.

The invention as disclosed hereinbelow has wide-reaching application, from separations to protective clothing to detection to electronics. The composites also are able to stabilize otherwise brittle polymers, such as polystyrene and poly(methyl methacrylate), such that the multi-layer structure formed by laminating composite layers can be stretched and/or bent, without compromise to the performance of the overall structure.

In an aspect of the present invention, there is provided a multi-layer structure comprising a first composite layer disposed over a second composite layer. The first composite layer comprises a first active material dispersed in a first polymer comprising an elastomeric polymer and the second composite layer comprises a second active material dispersed in a second polymer. The first active material and the second active material can be the same as or different from each other, and the first polymer and second polymer can be the same as or different from each other, such that the first composite layer and the second composite layer compositionally differ from each other in at least one respect, such as the nature of the active material, nature of the polymer or their amounts.

The first active material can be present in the first composite layer in any suitable amount, such as 1-99%, or 10-90%, or 20-80%, by weight or at least 15%, or at least 20%, or at least 30%, or at least 40%, or at least 50%, or at least 60%, or at least 70%, or at least 80% by weight, based on the total weight of the first active material and the first polymer. Similarly, the second active material can be present in the second composite layer in any suitable amount, such as 0-99%, or 10-90%, or 20-80%, by weight or at least 15%, or at least 20%, or at least 30%, or at least 40%, or at least 50%, or at least 60%, or at least 70%, or at least 80% by weight, based on the total weight of the first active material and the second polymer. In one embodiment, the second composite layer is free of second active material, i.e. the second composite layer does not contain any detectable amount of the second active material. Thus, as used herein, the term "second composite layer" does not imply that the second composite layer must be a composite material of a polymer and an active material; the second composite layer may or may not comprise the second active material.

In an embodiment, the first active material is present in the first composite layer in a concentration which is greater than or equal to the concentration of the second active material in the second composite layer. In another embodiment, the first active material is present in the first composite layer in a concentration which is less than or equal to the concentration of the second active material in the second composite layer.

In another aspect of the present invention, the multi-layer structure is a three-layer structure. The three-layer structure comprises a first composite layer disposed over a second composite layer and a third composite layer disposed over the first composite layer on a side of the multi-layer structure opposite the second composite layer, the third composite layer comprising a third active material dispersed in a third polymer. The third polymer can be the same as or different from the first polymer or the second polymer, and the third active material can be the same as or different from the first active material and the second active material.

In another aspect of the present invention, the multi-layer structure is a three-layer structure comprising a first composite layer disposed over a second composite layer and a third composite layer disposed over the second composite layer on a side of the multi-layer structure opposite the first composite layer, the third composite layer comprising a third active material dispersed in a third polymer. The third polymer can be the same as or different from the first polymer or the second polymer, and the third active material can be the same as or different from the first active material and the second active material.

In one embodiment of the three-layer structure, the concentration of the third active material in the third composite layer is equal to or less than the concentration of the first active material in the first composite layer. In another embodiment of the three-layer structure, the concentration of the third active material in the third composite layer is equal to or greater than the concentration of the first active material in the first composite layer.

In another aspect of the invention, an n-layer structure is provided, comprising one or more additional composite layer (i.e., composite layers in addition to the first and second composite layers)s, thereby resulting in an n-layer structure, wherein n=3 to 100. In one embodiment, the at least one of the one or more additional composite layers comprises an active material that is the same as or different from the first active material, the second active material, and/or the third active material.

In yet another embodiment of the multi-layer structures of the present invention, at least one of the second, the third and the one or more additional composite layers comprises an electrospun fiber or composite fiber comprising an MOF dispersed in a polymer.

In yet another embodiment of the multi-layer structures of the present invention, at least one of the first, the second, the third and the one or more additional composite layers comprises a mixture of two or more active materials. In such embodiments, each active material in the mixture of two or more active materials can chemically or physically interact with a different toxic chemical. For example, a mixture of two or more active materials may comprise a mixture of UiO-66-$NH_2$ and HKUST-1, where UiO-66-$NH_2$ is reactive towards CWAs and HKUST-1 is reactive towards a different toxic chemical, such as ammonia.

In an embodiment, the multi-layer structures further comprise one or more adhesive polymeric layers disposed in between and in contact with at least two layers of the first, the second, the third, and/or the additional composite layers. That is, adjacent composite layers in the multi-layer structure may be in direct contact with each other (preferably, in a manner such that the adjacent composite layers are directly bonded or attached to each other, whereby the multi-layer structure is resistant to delamination) or may be separated from each other by an adhesive polymeric layer (which functions to adhesively join the adjacent composite polymer layers). In certain embodiments, such an adhesive polymeric layer does not contain an active material. Any of the adhesive polymeric compositions known in the art may be used to form the adhesive polymeric layer, including for example hot melt adhesives and solvent-borne adhesives and adhesive polymeric compositions used as tie layers in the laminate film art.

Suitable active materials are selected from the group consisting of MOFs, metal oxides, metal hydroxides, zeolites, and combinations thereof.

MOFs are comprised of secondary building units (SBUs), typically made from metal oxide clusters, connected by organic linkers. The resulting structure is an extended, 3-dimensional framework that is often highly porous. Due to the ability to change/tune both the SBU (e.g., by changing metal type) and organic linker (e.g., by putting functional groups on the linker, and/or by using larger/bulkier/longer linkers), an incredibly broad range of structures is possible.

There are multiple sub-groups of MOFs, such as isoreticular MOFs (IRMOFs), UiO-MOFs, MIL MOFs, zeolitic imidazolate frameworks (ZIFs), porous coordination networks (PCNs), and others. Typically, these groups are based on similarities of the structures. For example, most of the IRMOFs contain zinc acetate SBUs, and changing the linker results in a wide range of porous structures. IRMOFs in particular are not stable to water, however.

UiO-66-type MOFs are structures that were originally synthesized at the University of Oslo. Comprised of zirconium-based SBUs, this series of MOFs is particularly stable when exposed to water or acidic conditions. UiO-66 utilizes a terephthalic acid (aka benzene dicarboxylate) linker that can be functionalized with a variety of groups, such as an amine (aka amino) group (herein known as UiO-66-$NH_2$). Organic linkers for some UiO-based MOFs are as follows:

UiO-66

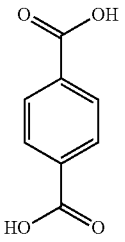

UiO-66-$NH_2$

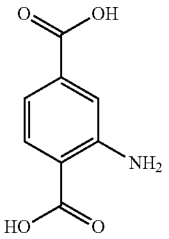

UiO-67

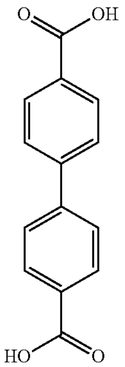

-continued

UiO-67-$NH_2$

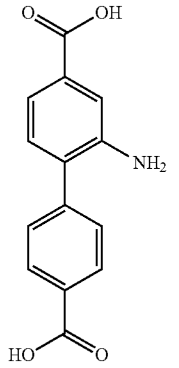

UiO-67-$N(Me)_2$

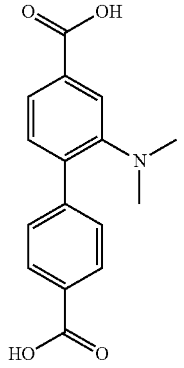

Other MOFs of interest include HKUST-1 (aka CuBTC, $Cu_3BTC_2$), a copper-based MOF linked by benzene tricarboxylate, and PCN-250, an iron-based MOF linked by diazo-based linkers. Both of these MOFs are undercoordinated, meaning metals are not completely linked and are available for sorption and reaction. Both MOFs are also able to interchange metals to some extent; copper can be replaced with zinc and other metals, and iron can be replaced by cobalt, manganese, nickel, and others.

In an embodiment, the MOF can be selected from the group consisting of zirconium-based MOFs, copper-based MOFs, iron-based MOFs, zinc-based MOFs and mixtures thereof. In another embodiment, the MOF is selected from the group consisting of UiO-66 (Zirconium 1,4-dicarboxybenzene MOF, $C_{48}H_{28}O_{32}Zr_6$), UiO-66-$NH_2$, UiO-66-X (where X=functional group), UiO-67, ZIF-8, HKUST-1, PCN-250, Cu-MOF-74, and mixtures thereof.

Any suitable metal oxide and/or metal hydroxide can be used as an active material, including, but not limited to, zirconium hydroxide, titanium oxide (titania), aluminum oxide (alumina), iron oxide, calcium oxide, magnesium oxide, and mixtures thereof.

Any suitable zeolite can be used as an active material, as long as the zeolite can chemically and/or physically interact with at least one toxic chemical. Such zeolites include, but are not limited to, alumina-silicates, ZSM-5, H-ZSM-5, Zeolite Beta, MCM-41, Zeolite A, Zeolite X, Zeolite Y, and mixtures thereof.

In yet another embodiment, at least one of the first composite layer, the second composite layer, the third composite layer and/or the additional composite layers further comprises at least one porous material selected from the group consisting of activated carbon, silicas, porous materials, catalysts, and the like. Exemplary porous materials include, but are not limited to, porous silicas, MCM-41, MCM-48, clay, BPL carbon, synthetic carbon, and coconut shell carbon. Exemplary catalysts include, but are not limited to, gold-based catalysts, silver-based catalysts, copper-based catalysts, and manganese-based catalysts.

According to certain embodiments, the active material is in the form of solid particles which are dispersed in a matrix of a polymer to provide a composite layer. The particle size of the active material may be tailored as appropriate to achieve a particular desired performance or other attributes in the composite layer. For example, the active material may have an average particle size of from 5 to 10,000 nm, or 10 to 5000 nm, or 25 to 1000 nm according to certain embodiments of the invention.

In an embodiment, the first polymer is an elastomeric polymer selected from the group consisting of elastomeric homopolymers, elastomeric block copolymers, elastomeric random copolymers, elastomeric graft copolymers, elastomeric brush copolymers, and elastomeric thermosets. In another embodiment, the first polymer is an elastomeric block copolymer selected from the group consisting of styrene-based block copolymers, methyl methacrylate-based block copolymers, and olefin-based block copolymers.

In another embodiment, the second polymer, and the third polymer are independently selected from the group consisting of thermoplastic homopolymers, thermoplastic block copolymers, thermoplastic random copolymers, thermoplastic graft copolymers, thermoplastic brush copolymers, elastomeric homopolymers, elastomeric block copolymers, elastomeric random copolymers, elastomeric graft copolymers, elastomeric brush copolymers, elastomeric thermosets, and combinations thereof. In an embodiment, the first polymer, the second polymer, and the third polymer exclude perfluoropolymers and polyalkylimines.

In another embodiment, the second polymer, and the third polymer are independently selected from the group consisting of polyethylene oxide (PEO), polystyrene (PS), poly (methyl methacrylate) (PMMA), poly(vinylidene fluoride) (PVDF), polystyrene-block-isoprene block-styrene (SIS), polystyrene-block-poly(ethylene-ran-butylene)-block-styrene (SEBS), styrene-butadiene rubber (SBR), polystyrene-block-butadiene-block-styrene (SBS), and blends thereof, excluding perfluoropolymers and polyalkylimines. In such embodiment, the elastomeric polymer is selected from the group consisting of SIS, SEBS, SBR, SBS, and blends thereof.

According to various embodiments of the present invention, any suitable elastomeric block copolymer may be used, including, but not limited to styrene-based block copolymers, methyl methacrylate-based block copolymers, olefin-based block copolymers, among others. As used herein the term "styrene-based block copolymers" is used interchangeably with "styrenic block copolymer". Styrenic block copolymers that are thermoplastic elastomers are especially suitable for use in the present invention. Suitable monomers could be used to form block copolymers, which can lead to new or substantially enhanced properties such as impact resistance, strain-at-break, toughness, solvent resistance, permeability, selectivity, transport, etc. In some cases, block copolymers allow the tuning multiple properties simultaneously (e.g., structural stability while also having stretchable properties).

Any of the styrenic block copolymers known in the art may be utilized in the present invention. Typically, such block copolymers comprise one or more (preferably, two or more) styrenic blocks (i.e., blocks of one or more vinyl aromatic monomers in polymerized form) which are relatively "hard" and one or more blocks which are relatively "soft", such as blocks of polymerized dienes such as butadiene or isoprene or blocks of hydrogenated polymerized dienes (which, in the case of butadiene may be referred to as ethylene-ran-butylene blocks). Suitable styrenic block copolymers include linear as well as radial, star, or branched styrenic block copolymers as well as gradient or tapered styrenic block copolymers. According to certain embodiments, a styrenic block copolymer is used which corresponds to the general structure A-$(B-A)_n$-B-A, where A is a styrenic block (e.g., a block of polystyrene) and B is a "soft" block (e.g., polymerized butadiene, polymerized isoprene, an ethylene-ran-butylene block), and n is an integer of 0-6. As is well known is the art, the composition of each block, the number of blocks, the arrangement of the blocks relative to each other, the molecular weight of each block, and the overall molecular weight of the styrenic block copolymer may be selected and tailored in order to fulfill the performance requirements which may be required or desired for a particular end-use application.

In an embodiment, the multi-layer structure of the present invention has a surface area of from 1 to 5,000, or 1 to 500, or 10 to 100 $m^2/g$.

In an embodiment, there is provided a two-layer structure selected from the group consisting of:

a) 40-60 wt % HKUST-1 in an SEBS block copolymer/40-60 wt % UiO-66-$NH_2$ in an SEBS block copolymer;
b) 40-60 wt % UiO-66-$NH_2$ in an SEBS block copolymer/40-60 wt % $Zr(OH)_4$ in an SEBS block copolymer; and
c) 10-30 wt % UiO-66-$NH_2$ in an SEBS block copolymer/70-90 wt % UiO-66-$NH_2$ in an SEBS block copolymer, wherein the amounts in wt % are based on the total weight of the active material and the polymer in each composite layer.

In another embodiment, there is provided a three-layer structure selected from the group consisting of:

(i) 10-30 wt % UiO-66-$NH_2$ in an SIS block copolymer/50-80 wt % HKUST-1 in an SIS block copolymer/10-30 wt % UiO-66-$NH_2$ in an SIS block copolymer;
(ii) 10-30 wt % HKUST-1 in an SIS block copolymer/50-80 wt % UiO-66-$NH_2$ in an SIS block copolymer/10-30 wt % HKUST-1 in an SIS block copolymer;
(iii) 10-30 wt % UiO-66-$NH_2$ in an SIS block copolymer/50-80 wt % HKUST-1 in a polystyrene/10-30 wt % UiO-66-$NH_2$ in an SIS block copolymer;
(iv) 10-30 wt % UiO-66-$NH_2$ in an SIS block copolymer/40-80 wt % HKUST-1 in a PEO/10-30 wt % UiO-66-$NH_2$ in an SIS block copolymer;
(v) 10-30 wt % UiO-66-$NH_2$ in an SIS block copolymer/50-80 wt % HKUST-1 in a poly(methyl methacrylate)/10-30 wt % UiO-66-$NH_2$ in an SIS block copolymer; and
(vi) 10-30 wt % UiO-66-$NH_2$ in an SEBS block copolymer/Electrospun 10-30 wt % UiO-66-$NH_2$-PVDF composite fiber/10-30 wt % UiO-66-$NH_2$ in an SEBS block copolymer, wherein the amounts in wt % are based on the total weight of the active material and the polymer in each composite layer.

In an embodiment, the multi-layer structure of the present invention is a layered mixed-matrix membrane. In another embodiment, the multi-layer structure of the present invention is a layered mixed-matrix composite.

In an aspect, the multi-layer structure of the present invention, as disclosed hereinabove, is used as a barrier layer against one or more toxic chemicals in an article selected from the group consisting of gloves, boots, clothing, gas masks, tents, filters, and sensors, wherein the one or more toxic chemicals comprise one or more of ammonia, chlorine, nitrogen dioxide, sulfur dioxide, carbon monoxide, chemical warfare agents, simulants, oils, contaminants, battlefield contaminants and combinations thereof.

In another aspect, a process of making the multi-layer structure or composite of the present invention is provided, comprising the step of mixing an active material with a polymer, optionally in an organic solvent, to form a coating composition and forming at least one of the composite layers by depositing the coating composition using one or more of drawn-down coating (doctor blading), spin-coating, dip-coating, spraying, extrusion, casting and electrospinning. The process can further include repeating the above steps to form an n-layered structure and optionally forming an adhesive polymeric layer in between and in contact with two composite layers.

In another aspect, a method for removing one or more toxic chemicals is provided. The method comprising the steps of providing a multi-layer structure as disclosed hereinabove, having an outer surface and an inner surface and contacting a feed stream comprising one or more toxic chemicals with the outer surface of the multi-layer structure to produce a toxic chemical-rich retentate stream and a permeate stream, such that the concentration of one or more toxic chemicals in the permeate stream is less than that present in the retentate stream. In such embodiment, the multi-layer structure allows transport of moisture vapor through at least one of the one or more composite layers. In an embodiment, at least one of the one or more toxic chemicals present in the permeate stream substantially reacts with and/or is adsorbed by the active material and/or substantially decomposes before reaching the inner surface of the multi-layer. The feed stream can be atmospheric air, water or a solution.

In yet another aspect, a method for decontaminating a surface contaminated with one or more toxic chemicals is provided. The method comprises the steps of contacting a multi-layer structure film according to the present disclosure, with a contaminated surface and removing the multi-layer structure film from the contaminated surface, thereby resulting in a decontaminated surface. In such embodiment, the decontaminated surface contains a lower amount of one or more toxic chemicals as compared to the contaminated surface. In an embodiment, the step of contacting a multi-layer structure with a contaminated surface further comprises providing a coating composition comprising an active material and a polymer, optionally dispersed in an organic solvent; and forming a multi-layer structure film over the contaminated surface by spraying or drop casting the coating composition over the contaminated surface. In another embodiment, the step of contacting a multi-layer structure with a contaminated surface further comprises forming a mixed-matric membrane film by co-extruding a composition comprising an active material and a polymer.

In another aspect, a method for sensing one or more toxic chemicals is provided, comprising the steps of providing a multi-layer structure according to the present disclosure, having an outer surface and an inner surface and contacting a feed stream comprising one or more toxic chemicals with the outer surface of the multi-layer structure to produce a toxic chemical-rich retentate stream and a permeate stream.

The method further comprises a step of sensing the one or more toxic chemicals in the feed stream by one or more of colorimetric changes, spectral changes, electrical impedance changes, resistive changes, and the like. In such embodiments, the one or more toxic chemicals comprise at least one toxic chemical selected from the group consisting of ammonia, chlorine, nitrogen dioxide, sulfur dioxide, carbon monoxide, chemical warfare agents, simulants, oils, contaminants, battlefield contaminants, and combinations thereof.

In another aspect, a method for separating gases is provided, comprising the steps of providing a multi-layer structure according to the present disclosure, having an outer surface and an inner surface and contacting a feed stream comprising a mixture of two or more gases, with the outer surface of the multi-layer structure to produce a first gas-rich retentate gas stream and a second gas-rich permeate gas stream, thereby separating the gas mixture into two separate gases.

In an embodiment of the method for separating gases, the feed stream is a mixture of three gases, for example gas A, gas B and gas C. In such embodiment, the step of contacting the feed stream with the outer surface of the multi-layer structure produces a gases A&B-rich retentate gas stream and a gas C-rich permeate gas stream. The method can further include contacting the gases A&B-rich retentate gas stream with the outer surface of another multi-layer structure, according to the present disclosure, to produce a gas A-rich retentate gas stream and a gas B-rich permeate gas stream.

In an embodiment the feed stream may include one or more of oxygen, nitrogen, carbon dioxide, and methane.

Each layer of the n-layered multi-layer structure of the present disclosure can have any suitable thickness, which may depend upon the end-use. For example, a sensor may comprise a multi-layer structure can have a thickness in the range of less than 1 micron or less than 0.5 microns or less than 0.1 microns. On the other hand, the multi-layer structure for use as a barrier layer may be much thicker, having a thickness of at most 20 mils (508 microns), or 10 mils (254 microns), or 5 mils (127 microns). In one embodiment, the multi-layer structure can have a thickness in the range of 0.1 to 600 microns or from 0.1 to 300 microns, or from 75 to 250 microns. The thicknesses of the individual composite layers within the multi-layer structure may also be varied as may be desired or appropriate depending upon factors such as the compositions of the composite layers and the intended end-use for the multilayer structure. The thicknesses of each of the composite layers may be the same as or different from each other.

Aspects of the Invention

Certain illustrative, non-limiting aspects of the invention may be summarized as follows:

Aspect 1: A multi-layer structure comprising:

a first composite layer disposed over a second composite layer, wherein the first composite layer comprises 1-99% by weight of a first active material dispersed in a first polymer comprising an elastomeric polymer and the second composite layer comprises 0-99% by weight of a second active material dispersed in a second polymer, wherein the first active material chemically or physically interacts with at least one toxic chemical and is selected from the group consisting of MOFs, metal oxides, metal hydroxides, zeolites and combinations thereof, and wherein the first active material and the second active material are the same as or different from each other, and the first polymer and second polymer are the same as or different from each other, subject to the proviso that the first composite layer and the second composite layer compositionally differ from each other in at least one respect.

Aspect 2: The multi-layer structure according to aspect 1, wherein the elastomeric polymer is selected from the group consisting of elastomeric homopolymers, elastomeric block copolymers, elastomeric random copolymers, elastomeric graft copolymers, elastomeric brush copolymers, and elastomeric thermosets.

Aspect 3: The multi-layer structure according to claim 2, wherein the elastomeric polymer Is an elastomeric block copolymer selected from the group consisting of styrene-based block copolymers, methyl methacrylate-based block copolymers, and olefin-based block copolymers.

Aspect 4: The multi-layer structure according to aspect 1, wherein the first active material is present in the first composite layer in a concentration which is greater than or equal to the concentration of the second active material in the second composite layer.

Aspect 5: The multi-layer structure according to aspect 1, wherein the first active material is present in the first composite layer in a concentration which is less than or equal to the concentration of the second active material in the second composite layer.

Aspect 6: The multi-layer structure according to aspect 1, wherein the first active material is a MOF present in an amount of at least 15%, or at least 20%, or at least 30%, or at least 40%, or at least 50%, or at least 60%, or at least 70%, or at least 80% by weight, based on the total weight of the MOF and the first polymer.

Aspect 7: The multi-layer structure according to any of aspects 1-6, further comprising a third composite layer disposed over the first composite layer on a side of the multi-layer structure opposite the second composite layer, wherein the third composite layer comprises a third active material dispersed in a third polymer, wherein the third polymer is the same as or different from the first polymer or the second polymer, and wherein the third active material is the same as or different from the first active material and the second active material.

Aspect 8: The multi-layer structure according to any of aspects 1-6, further comprising a third composite layer disposed over the second composite layer on a side of the multi-layer structure opposite the first composite layer, wherein the third composite layer comprises a third active material dispersed in a third polymer, wherein the third polymer is the same as or different from the first polymer or the second polymer, and wherein the third active material is the same as or different from the first active material and the second active material.

Aspect 9: The multi-layer structure according to aspect 7 or 8, wherein the concentration of the third active material in the third composite layer is equal to or less than the concentration of the first active material in the first composite layer.

Aspect 10: The multi-layer structure according to aspect 7 or 8, wherein the concentration of the third active material in the third composite layer is equal to or greater than the concentration of the first active material in the first composite layer.

Aspect 11: The multi-layer structure according to any of aspects 1-10, further comprising one or more additional composite layers, thereby resulting in an n-layer structure, wherein n=3 to 100.

Aspect 12: The multi-layer structure according to aspect 11, wherein at least one of the one or more additional composite layers comprises an active material that is the same as or different from the first active material, the second active material, and/or the third active material.

Aspect 13: The multi-layer structure according to any of aspects 1-12, wherein at least one of the second, the third and the one or more additional composite layers comprises an electrospun fiber or composite fiber comprising an MOF dispersed in a polymer.

Aspect 14: The multi-layer structure according to any of aspects 1-13, wherein at least one of the first, the second, the third and the one or more additional composite layers comprises a mixture of two or more active materials, and wherein each active material in the mixture of two or more active materials chemically or physically interacts with a different toxic chemical.

Aspect 15: The multi-layer structure according to any of aspects 1-14, wherein each of the first active material, the second active material, the third active material and the mixture of two or more active materials comprises at least one MOF independently selected from the group consisting of zirconium-based MOFs, copper-based MOFs, iron-based MOFs, zinc-based MOFs, and mixtures thereof.

Aspect 16: The multi-layer structure according to any of aspects 1-14, wherein the MOF is selected from the group consisting of UiO-66, UiO-66-$NH_2$, UiO-66-X (where X=functional group), UiO-67, ZIF-8, HKUST-1, PCN-250, Cu-MOF-74 and mixtures thereof.

Aspect 17: The multi-layer structure according to any of aspects 1-15, wherein the second polymer and the third polymer are independently selected from the group consisting of thermoplastic homopolymers, thermoplastic block copolymers, thermoplastic random copolymers, thermoplastic graft copolymers, thermoplastic brush copolymers, elastomeric homopolymers, elastomeric block copolymers, elastomeric random copolymers, elastomeric graft copolymers, elastomeric brush copolymers, elastomeric thermosets and combinations thereof, excluding perfluoropolymers and polyalkylimines.

Aspect 18: The multi-layer structure according to any of aspects 1-16, wherein the second polymer, and the third polymer are independently selected from the group consisting of poly(ethylene oxide) (PEO), polystyrene (PS), poly (methyl methacrylate) (PMMA), poly(vinylidene fluoride) (PVDF), polystyrene-block-isoprene-block-styrene (SIS), polystyrene-block-poly(ethylene-ran-butylene)-block-styrene (SEBS), styrene-butadiene rubber (SBR), polystyrene-block-butadiene-block-styrene (SBS), and blends thereof, and wherein the first polymer is selected from the group consisting of SIS, SEBS, SBR, SBS, and blends thereof.

Aspect 19: The multi-layer structure according to any of aspects 1-18, wherein the multi-layer structure has a surface area of from 1 to 5,000 $m^2/g$.

Aspect 20: The multi-layer structure according to any of aspects 1-19, further comprising one or more adhesive polymeric layers disposed in between and in contact with at least two of the first, the second, the third, and/or the additional composite layers.

Aspect 21: The multi-layer structure according to any of aspects 1-20, wherein at least one of the first composite layer, the second composite layer, the third composite layer and/or the additional composite layers further comprises at least one porous material selected from the group consisting of activated carbon, silicas, porous materials, and catalysts.

Aspect 22: The multi-layer structure according to any of aspects 1-21, wherein the at least one toxic chemical comprises one or more toxic chemicals selected from the group consisting of ammonia, chlorine, nitrogen dioxide, sulfur dioxide, carbon monoxide, chemical warfare agents, simulants, oils, contaminants, battlefield contaminants, and combinations thereof.

Aspect 23: The multi-layer structure according to any of aspects 1-6, wherein the multi-layer structure is selected from the group consisting of:

(i) 40-60 wt % HKUST-1 in an SEBS block copolymer/40-60 wt % UiO-66-$NH_2$ in an SEBS block copolymer;

is (ii) 40-60 wt % UiO-66-$NH_2$ in an SEBS block copolymer/40-60 wt % $Zr(OH)_4$ in an SEBS block copolymer; and (iii) 10-30 wt % UiO-66-$NH_2$ in an SEBS block copolymer/70-90 wt % UiO-66-$NH_2$ in an SEBS block copolymer, wherein the amounts in wt % are based on the total weight of the active material and the polymer in each composite layer.

Aspect 24: The multi-layer structure according to any of aspects 5-9, wherein the multi-layer structure is a three-layer structure selected from the group consisting of:

(i) 10-30 wt % UiO-66-$NH_2$ in an SIS block copolymer/50-80 wt % HKUST-1 in an SIS block copolymer/10-30 wt % UiO-66-$NH_2$ in an SIS block copolymer;

(ii) 10-30 wt % HKUST-1 in an SIS block copolymer/50-80 wt % UiO-66-$NH_2$ in an SIS block copolymer/10-30 wt % HKUST-1 in an SIS block copolymer;

(iii) 10-30 wt % UiO-66-$NH_2$ in an SIS block copolymer/50-80 wt % HKUST-1 in a polystyrene/10-30 wt % UiO-66-$NH_2$ in an SIS block copolymer;

(iv) 10-30 wt % UiO-66-$NH_2$ in an SIS block copolymer/40-80 wt % HKUST-1 in a PEO/10-30 wt % UiO-66-$NH_2$ in an SIS block copolymer;

(v) 10-30 wt % UiO-66-$NH_2$ in an SIS block copolymer/50-80 wt % HKUST-1 in a poly(methyl methacrylate)/10-30 wt % UiO-66-$NH_2$ in an SIS block copolymer; and (vi) 10-30 wt % UiO-66-$NH_2$ in an SEBS block copolymer/electrospun 10-30 wt % UiO-66-$NH_2$-PVDF composite fiber/10-30 wt % UiO-66-$NH_2$ in an SEBS block copolymer, wherein the amounts in wt % are based on the total weight of the active material and the polymer in each composite layer.

Aspect 25: The multi-layer structure according to any of aspects 1-24, wherein the multi-layer structure is a multi-layer mixed-matrix membrane or a multi-layer mixed-matrix composite.

Aspect 26: Use of the multi-layer structure according to any of aspects 1-25 as a barrier layer against one or more toxic chemicals in an article selected from the group consisting of gloves, boots, clothing, gas masks, tents, filters, and sensors, wherein the one or more toxic chemicals comprise one or more of ammonia, chlorine, nitrogen dioxide, sulfur dioxide, carbon monoxide, chemical warfare agents, simulants, oils, contaminants, battlefield contaminants, and combinations thereof.

Aspect 27: A process for making the multi-layer structure according to any of aspects 1-25, comprising:

(i) mixing an active material with a polymer, optionally in an organic solvent, to form a coating composition;

(ii) forming at least one of the composite layers by depositing the coating composition using one or more methods selected from the group consisting of drawn-down coating (doctor blading), spin-coating, dip-coating, spraying, extrusion, casting, and electrospinning;

(iii) repeating steps (i) and (ii) to form an n-layer structure; and (iv) optionally forming an adhesive polymeric layer in between and in contact with two composite layers.

Aspect 28: A method for removing one or more toxic chemicals comprising the steps of:

(i) providing a multi-layer structure according to any of aspects 1-25, having an outer surface and an inner surface; and (ii) contacting a feed stream comprising one or more toxic chemicals with the outer surface of the multi-layer structure to produce a toxic chemical-rich retentate stream and a permeate stream, wherein the concentration of one or more toxic chemicals in the permeate stream is less than that present in the retentate stream.

Aspect 29: The method according to aspect 28, wherein the multi-layer structure allows transport of moisture vapor through at least one of the one or more composite layers.

Aspect 30: The method according to either of aspects 28 or 29, wherein the one or more toxic chemicals comprises at least one toxic chemical selected from the group consisting of ammonia, chlorine, nitrogen dioxide, sulfur dioxide, carbon monoxide, chemical warfare agents, simulants, oils, contaminants, battlefield contaminants, and combinations thereof.

Aspect 31: The method according to any of aspects 28-30, wherein at least one of the one or more toxic chemicals present in the permeate stream substantially reacts with the active material and/or substantially decomposes before reaching the inner surface of the multi-layer structure.

Aspect 32: The method according to any of aspects 28-31, wherein the feed stream comprises atmospheric air, water or a solution.

Aspect 33: A method for decontaminating a surface contaminated with one or more toxic chemicals, comprising the steps of:

a) contacting a multi-layer structure film according to any of aspects 1-25 with a contaminated surface;

b) removing the multi-layer structure film from the contaminated surface, thereby resulting in a decontaminated surface.

wherein the decontaminated surface contains a lower amount of one or more toxic chemicals as compared to the contaminated surface.

Aspect 34: The method of aspect 33, wherein the step of contacting a multi-layer structure with a contaminated surface further comprises:

(i) providing a coating composition comprising an active material and a polymer, optionally dispersed in an organic solvent; and (ii) forming a mixed-matric membrane film over the contaminated surface by spraying or drop casting the coating composition over the contaminated surface.

Aspect 35: The method of aspect 33, wherein the step of contacting a multi-layer structure with a contaminated surface further comprises forming a multi-layer structure film by co-extruding a composition comprising an active material and a polymer.

Aspect 36: A method for sensing one or more toxic chemicals comprising the steps of:

(i) providing a multi-layer structure according to any of aspects 1-25, having an outer surface and an inner surface;

(ii) contacting a feed stream comprising one or more toxic chemicals with the outer surface of the multi-layer structure to produce a toxic chemical-rich retentate stream and a permeate stream; and (iii) sensing the one or more toxic chemicals in the feed stream by one or more of colorimetric changes, spectral changes, electrical impedance changes, resistive changes, and the like, wherein the one or more toxic chemicals comprise at least one toxic chemical selected from the group consisting of ammonia, chlorine, nitrogen dioxide, sulfur dioxide, carbon monoxide, chemical warfare agents, simulants, oils, contaminants, battlefield contaminants and combinations thereof.

Aspect 37: A method for separating gases comprising the steps of:

(i) providing a multi-layer structure of any of aspects 1-25, having an outer surface and an inner surface; and (ii) contacting a feed stream comprising a mixture of two or more gases, with the outer surface of the multi-layer structure to produce a first gas-rich retentate gas stream and a second gas-rich permeate gas stream, thereby separating the gas mixture into two separate gases.

Aspect 38: The method of aspect 36 wherein the feed stream comprises a mixture of three gases: gas A, gas B and gas C, wherein the step of contacting the feed stream with the outer surface of the multi-layer structure produces a gases A&B-rich retentate gas stream and a gas C-rich permeate gas stream, and wherein the method further comprises contacting the gases A&B-rich retentate gas stream with the outer surface of another multi-layer structure of any of aspects 1-23 to produce a gas A-rich retentate gas stream and a gas B-rich permeate gas stream.

Aspect 39: The method of aspects 37 or 38, wherein the feed stream comprises one or more gases selected from the group consisting of oxygen, nitrogen, carbon dioxide, and methane.

As used herein, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

Within this specification, embodiments have been described in a way which enables a clear and concise specification to be written, but it is intended and will be appreciated that embodiments may be variously combined or separated without departing from the invention. For example, it will be appreciated that all preferred features described herein are applicable to all aspects of the invention described herein.

In some embodiments, the invention herein can be construed as excluding any element or process step that does not materially affect the basic and novel characteristics of the multi-layer structures and processes for making or using such multi-layer structures. Additionally, in some embodiments, the invention can be construed as excluding any element or process step not specified herein.

EXAMPLES

Examples of the present invention will now be described. The technical scope of the present invention is not limited to the examples described below.

Experimental Methods

Figure 3:
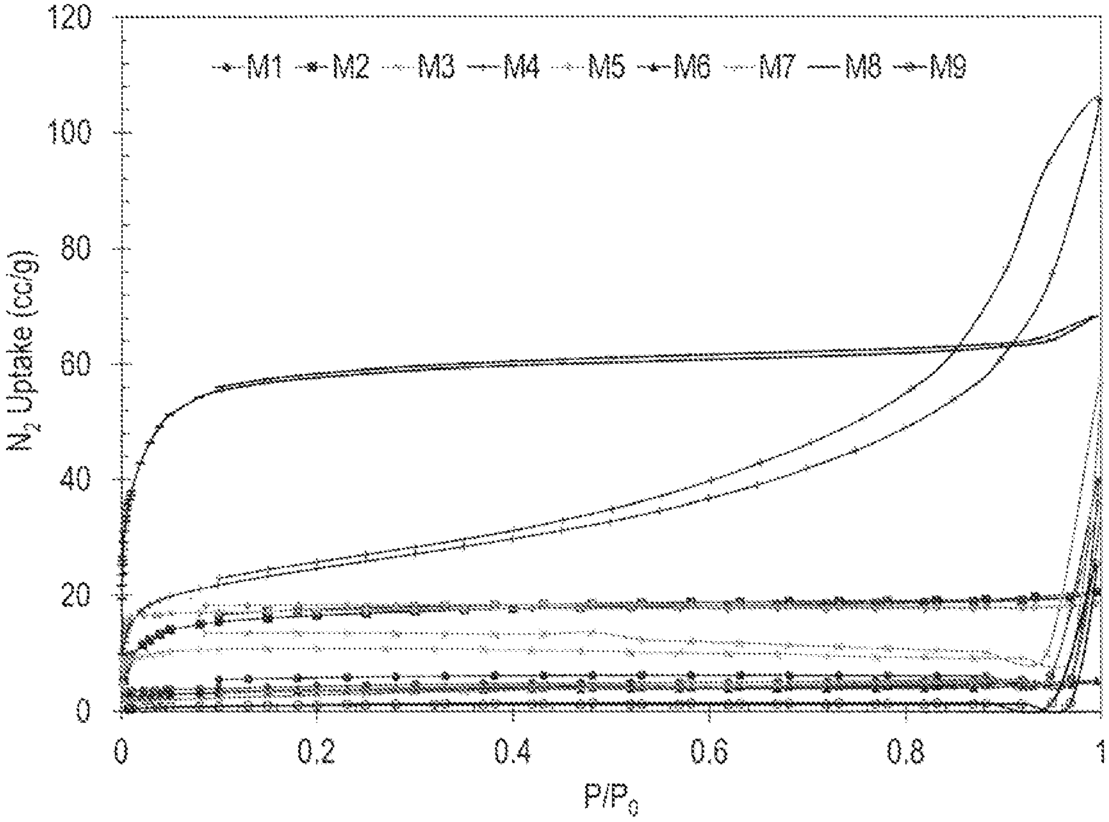
FIG. 3 shows nitrogen uptake as a function of relative pressure for the two- and three-layer structures (M1-M9) of FIG. 2, whose compositions are defined in Table 1 and Table 2.

Nitrogen isotherm. Nitrogen isotherms were measured using a Micromeritics ASAP 2040 analyzer at 77 K. Samples were off-gassed at 50° C. under vacuum for approximately 16 h. The relatively low temperature was used to prevent any adverse effects between the polymer and MOF within the MMC. The BET method was used to calculate specific surface area in $m^2/g$, and the t-plot method was used to calculate pore volume in $cm^3/g$. Nitrogen uptake data are shown in FIG. 3, and surface areas and pore volumes are shown in Table 3.

Scanning Electron Microscopy and Energy Dispersive X-ray Spectroscopy (EDS). SEM images were obtained using a Phenom GSR desktop SEM. Samples were submerged in liquid nitrogen and cracked to form a clean break, and then mounted on double-sided carbon tape with the cracked edge facing upwards. EDS was used for elemental mapping of the MOFs within the composites and was conducted at an accelerating voltage of 15 kV.

Figure 4:
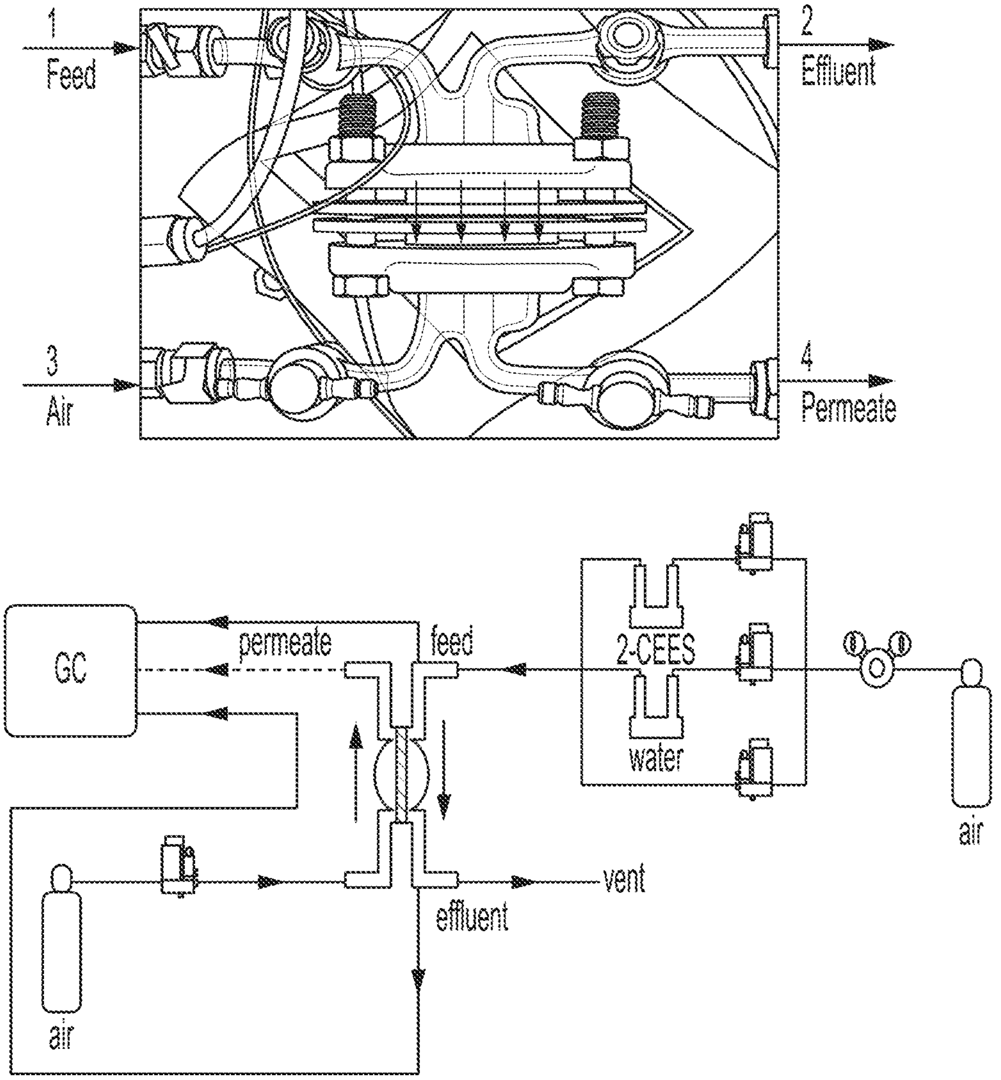
FIG. 4 shows a permeation test cell (left) and permeation piping and instrumentation diagram (right).

Permeation. 2-chloroethyl ethyl sulfide (CEES) and bis 2-chloroethyl sulfide (distilled mustard) permeation testing was conducted in accordance with ASTM F739-12. Briefly, a 1.5"×1.5" film was cut, weighed, and measured for thickness with a micrometer caliper and placed in a 1-inch-diameter Pesce PTC 700 permeation test cell. An equal countercurrent flow of 0% relative humidity and 300 (RH) mL $min^{-1}$ air was applied to both sides of the swatch with a feed side concentration of 300 $mg/m^3$ CEES. The CEES concentration was monitored at 3 locations in the PTC 700 cell: the inlet stream to the cell apparatus (designated as the feed line), the outlet stream from the cell apparatus (designated as the effluent line), and the outlet stream from the cell apparatus on the opposite side of the swatch (designated as the permeate line). A schematic is shown in FIG. 4. As shown in FIG. 4, the MMM was placed in the center of the glass cell which was then tightened. Contaminated air streams flowed into the cell in the top left and out of the cell in the top right. A diluent stream entered the bottom left and exited the bottom right. Detectors were placed in the streams to monitor 2-CEES and mustard concentrations. The test was considered complete when the two outlet stream concentrations summed to equal the value of the feed concentration, closing the mass balance and satisfying the condition of equation 1.

$$C_{feed}-C_{effluent}-C_{permeate}=0 \quad (1)$$

Adsorption Isotherms. Pure-component isotherms of carbon dioxide ($CO_2$), methane ($CH_4$), nitrogen ($N_2$), and oxygen ($O_2$) were measured on a Micromeritics 3Flex 3500 instrument from 0 to 1 bar at room temperature. Prior to measurement, approximately 300 mg of sample was off-gassed at 50° C. under vacuum. $CO_2/N_2$ separation factors approximating flue gas concentrations were calculated from pure-component isotherms. The equation used was:

$$\alpha = \frac{n_{CO_2} P_{N_2}}{n_{N_2} P_{CO_2}} \quad (2)$$

in which α is the selectivity, $P_{N2}$ and $P_{CO2}$ are 0.75 bar and 0.15 bar respectively, and $n_{N2}$ and $n_{CO2}$ are the adsorbed quantities of each gas at the respective pressures. Nuclear Magnetic Resonance (NMR) Spectroscopy. $^{31}P$ magic angle spinning (MAS) NMR spectroscopy was used to measure the disappearance of soman and VX nerve agents into MMCs. Measurements were made using a Varian INOVA 400 Narrow Bore spectrometer equipped with a Doty Scientific solid-state probe. For soman tests, 3.5 μL was dispersed drop-wise on a 35 mg MMC. MAS was conducted at 1440 Hz. For VX, 4.5 μL was dispersed drop-wise on a 45 mg MMC with MAS conducted at 2400 Hz. Electrical Impedance Spectroscopy (EIS). EIS measurements were collected using a Solartron Analytical 1260 equipped with a 1296 dielectric interface and parallel plate sample holder. The voltage was set at 100 mV (alternating current) with a frequency sweep range from $10^{-2}$ to $10^6$ Hz.

Moisture Vapor Transport Rate (MVTR). MVTR measurements through the swatches were conducted in accordance with the Water Method outlined in ASTM E-96-16. Briefly, a swatch of material was sealed over a 1.75 in-diameter container filled to a headspace of 0.5 in with distilled water and placed in an environmentally-controlled chamber at 25° C. and 50% RH for 24 h. The total mass of the apparatus was weighed before and after the exposure, and the mass difference was divided by the cross-sectional area of the top of the container and the exposure time to generate a MVTR value. The MVTR value was reported in units of grams of water lost per square meter of surface area exposed to the humidity gradient in the test system per hour of exposure time. MVTR data are shown in Table 4.

Materials

All MOFs and metal hydroxides were obtained from NuMat Technologies, Inc. and Guild Associates, Inc., respectively. Tetrahydrofuran (THF) (99.5% purity), chloroform (99.5% purity), poly(ethylene oxide) (PEO), poly (vinylidene fluoride) (PVDF), polystyrene (PS), poly(methyl methacrylate) (PMMA), and polystyrene-block-polyisoprene-block-polystyrene (SIS) (20 wt % styrene) were obtained from Sigma Aldrich. SEBS G1642 and SEBS G1642*(20% Polystyrene) were obtained from Kraton Corporation.

Multi-Layer Structure

The multi-layer approach to flexible mixed-matrix membranes and flexible mixed-matrix composites has been demonstrated using an MOF chosen from either HKUST-1 or UiO-66-$NH_2$ MOFs or a metal oxide and/or hydroxide such as $Zr(OH)_4$, dispersed in a styrenic block copolymer such as an SIS copolymer, where at least one of the composite layer contains a high MOF loading (such as above 30 weight % or above 50 weight % or above 70 weight %). SIS is a well-known elastomer that provides an excellent combination of strength and elasticity, and is readily processable. The two MOFs, HKUST-1 or UiO-66-$NH_2$, were chosen as they have been shown to provide significant protection against toxic chemicals such as CWAs, ammonia, chlorine, and nitrogen dioxide. Furthermore, HKUST-1 and UiO-66-$NH_2$ are produced in sufficient quantities such that structure-activity-processing relationships can be readily studied at scales larger than typically available for most MOFs synthesized in sub-gram quantities. The details of these composites as well as a much wider array of configurations, chemistries, and various MMM constructs, are described in Table 1 and Table 2. In particular, Table 1 summarizes compositions of three-layer mixed-matrix membranes and Table 2 summarizes two-layer mixed-matrix membranes. The percentages represent the wt % MOF relative to polymer within each layer of the composite layer.

As shown in FIG. 1C, a composite layer in the form of an MOF/polymer film was cast using a draw-down coating method. Before the film completely dried, a second composite layer was drawn across the first layer. The solvent locally swelled or dissolved polymer chains, fusing the layers together, and the resulting layered structure could not be mechanically separated. This approach was repeated any number of times using a broad range of compositions to create multi-layered structures.

Fabricated multi-layer structures were characterized using techniques including scanning electron microscopy (SEM), energy dispersive X-ray spectroscopy (EDS), powder X-ray diffraction (PXRD) and nitrogen adsorption. The performance of MMCs as barriers against CWAs and simulants was evaluated through permeation experiments, and the reactivity of various composites was monitored using $^{31}P$ magic angle spinning nuclear magnetic resonance (MAS NMR) spectroscopy. Moisture vapor transport rate (MVTR) measurements were conducted to determine the permeability of each multi-layer structure to moisture. The multi-layer structures also were characterized for other applications, such as sensors, using gas adsorption isotherms and electrical impedance spectroscopy (EIS). Experimental details are provided in the supporting information.

Three-Layer Structure M1 (20 wt % UiO-66-$NH_2$ in SIS)/(67 wt % HKUST-1 in SIS)/(20 wt % UiO-66-$NH_2$ in SIS)

The MOF (or metal oxide) first was mixed with tetrahydrofuran (THF) at amounts necessary to achieve the target wt %. For example, M1 was made using three separate MOF/polymer mixtures. In the first mixture, 0.25 g UiO-66-$NH_2$ MOF was mixed with 5 mL THF and then tip-sonicated for 30 s. Next 1 g SIS was added. The mixture was vortexed and then was magnetically stirred at room temperature for approximately 16 h. In the second mixture, 2.0 g HKUST-1 MOF was mixed with 5 mL THF. After sonication, 1 g SIS was added, and the mixture was magnetically stirred for approximately 16 h. The third mixture was prepared in an identical manner to the first mixture.

After approximately 16 h of mixing, the first mixture was poured onto a Teflon block, and a film was drawn using a National Institute of Standards and Technology (NIST)-certified 10 mil blade. The film was allowed to dry for approximately 1 min, which was before the film was completely dry, the second mixture was poured on top of the first film. The same NIST-certified 10 mil blade was used to draw down the film. The solvent locally swelled or dissolved polymer chains, fusing the layers together, and the resulting layered structure could not be mechanically separated. This step was repeated using the third mixture resulting in M1, a three-layer structure or a layered mixed matrix composite (MMC) with two outer layers of 20 wt % UiO-66-$NH_2$ in SIS encasing a layer comprised of 67 wt % HKUST-1 in SIS.

Two-Layer and Three-Layer Structures, M2-M9

Each subsequent multi-layer structure was prepared using a similar procedure, as was used for the preparation of M1. All polymer solutions were 20% w/v (solvent basis) except for M6 and M9. Due to the limited solubility of PEO, a 5% w/v in chloroform (Sigma Aldrich, 99.5% purity) was used.

Figures 5A, 5B, 5C, 5D, 5E, 5F:
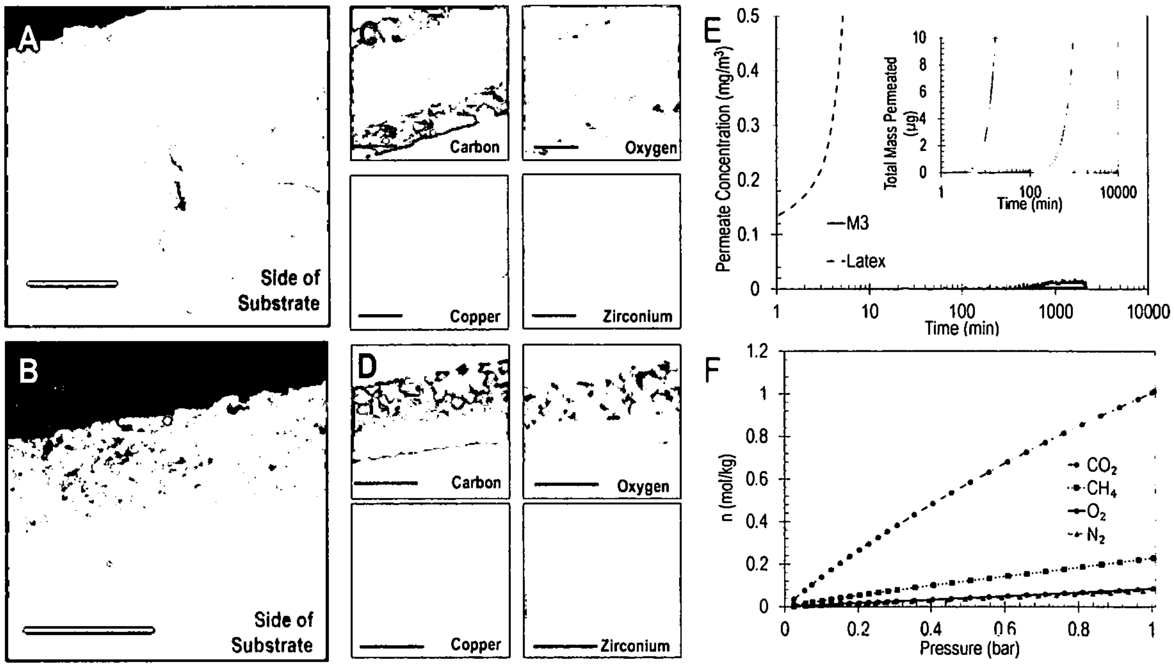
FIGS. 5A and 5B shows SEM images and FIGS. 5C and 5D shows corresponding Energy Dispersive X-ray Spectroscopy (EDS) maps of three-layer structure M1 and two-layer structure M3, respectively.
FIG. 5E shows 2-CEES permeation data through M3 and latex. The inset shows the total mass permeated through each material.
FIG. 5F shows Adsorption isotherms of M3 for $CO_2$, $CH_4$, $O_2$, and $N_2$ showing loading (n) as a function of pressure. Scale bar=100 μm in all images.

M3 exhibited a well-defined two-layer structure as shown in FIGS. 5B and 5D.

Two-Layer Structure, M8 with High Loading of MOF

The multi-layer structure concept of the present invention is demonstrated by M8 to having one composite layer with a high loading of MOF.

M8 was fabricated with a layer of 80 wt % UiO-66-$NH_2$ in SEBS and a protective layer of 20 wt % UiO-66-$NH_2$ in SEBS, using the procedure as described hereinabove. The resulting multi-layer structure M8 had the highest surface area of all MMCs studied (226 $m^2/g$), as summarized in Table 3.

Three-Layer Structure, M9 Comprising an Electrospun MOF Composite Nanofiber

An alternate polymer form factor in the form of PVDF nanofibers was also placed within the layered matrix and is referred to as M9. For the multi-layer structure, M9, an electrospun nanofiber was used as the middle composite layer of the three-layer structure.

First PVDF and UiO-66-$NH_2$ were mixed together to form a 80/20 solution and stirred. The amount of UiO-66-$NH_2$ was 40 wt % in the mixture (UiO-66-$NH_2$ mass to total mass) and then the mixture of PVDF and UiO-66-$NH_2$ was added to a 80/20 dimethylformamide/acetone solution. Composite fibers of PVDF and UiO-66-$NH_2$ were electrospun using an electrospinning nanofiber preparation system, MSK-NFES-4 floor unit (MTI Corporation), according to previously reported methods.[1] Electrospinning was conducted at 40° C., 15.5 kV, and 1 mL/h through an 18.5-gauge needle. Fibers were collected on a mandrel rotating at 300 rpm. After spinning, the resulting MOF/nanofiber composite was sandwiched between two SEBS/UiO-66-$NH_2$ (20%) layers to form M9.

This concept demonstrates the potential to utilize not only a wide range of polymers, but also, a wide range of polymeric structural forms.

TABLE 1

List of Prepared Three-Layer Structures (Mixed-Matrix Composites).

| | Three-layer Structures | | | | | |
|---|---|---|---|---|---|---|
| | 1st Composite layer | | 2nd Composite layer | | 3rd Composite layer | |
| Sample | 1st Polymer | 1st Active | 2nd Polymer | 2nd Active | 3rd Polymer | 3rd Active |
| M1 | SIS | 20 wt % UiO-66-$NH_2$ | SIS | 67 wt % HKUST-1 | SIS | 20 wt % UiO-66-$NH_2$ |
| M2 | SIS | 20 wt % HKUST-1 | SIS | 67 wt % UiO-66-$NH_2$ | SIS | 20 wt % HKUST-1 |
| M5 | SIS | 20 wt % UiO-66-$NH_2$ | Polystyrene | 67 wt % HKUST-1 | SIS | 20 wt % UiO-66-$NH_2$ |
| M6 | SIS | 20 wt % UiO-66-$NH_2$ | PEO | 67 wt % HKUST-1 | SIS | 20 wt % UiO-66-$NH_2$ |
| M7 | SIS | 20 wt % UiO-66-$NH_2$ | Poly(methyl methacrylate) | 67 wt % HKUST-1 | SIS | 20 wt % UiO-66-$NH_2$ |
| M9 | SEBS G1642 | 20 wt % UiO-66-$NH_2$ | Electrospun PVDF fiber | 20 wt % UiO-66-$NH_2$ | SEBS G1642 | 20 wt % UiO-66-$NH_2$ |

TABLE 2

List of Prepared Two-Layer Structures (Mixed-Matrix Composites).

| | Two-layer Structures | | | |
|---|---|---|---|---|
| | 1st Composite layer | | 2nd Composite layer | |
| Sample | 1st Polymer | 1st Active | 2nd Polymer | 2nd Active |
| M3 | SEBS G1642* | 50 wt % HKUST-1 | SEBS G1642 | 50 wt % UiO-66-$NH_2$ |
| M4 | SEBS G1642 | 50 wt % UiO-66-$NH_2$ | SEBS G1642 | 50 wt % $Zr(OH)_4$ |
| M8 | SEBS G1642 | 20 wt % UiO-66-$NH_2$ | SEBS G1642 | 80 wt % UiO-66-$NH_2$ |

*20 wt % polystyrene

SEM and EDS images confirmed the delineation of each layer (FIGS. 2, 5A-5D) in the multi-layer structures. The low MOF-loaded outer layers formed protective borders around the high MOF-loaded layers, which otherwise cracked without the encasing layer.

Surface Area Measurement of M1-M9

Nitrogen uptake data of M1-M9 are shown in FIG. 3, and surface area calculations are shown in Table 3.

TABLE 3

Surface area measurements for M1-M9.

| Sample | BET Surface Area ($m^2$/g) | Pore Volume ($cm^3$/g) |
|---|---|---|
| M1 | 16 | 0.00 |
| M2 | 65 | 0.02 |
| M3 | 42 | 0.02 |
| M4 | 87 | 0.01 |
| M5 | 73 | 0.02 |
| M6 | 13 | 0.00 |
| M7 | 11 | 0.00 |
| M8 | 226 | 0.09 |
| M9 | 4 | 0.00 |

All multi-layer structures M1-M9 had significantly lower surface area in comparison to the pristine MOFs. The relatively low surface area is typical for such structures, as nitrogen is unable to penetrate deeply into the composite layers, unless high MOF loadings are used. It should be noted that the multi-layer structures M1-M5 are not true mixed-matrix membranes as surface defects may increase nitrogen access to the MOF and govern permeation behavior; yet, it is possible to seal an active layer with high MOF loading with a low (<5%) MOF/polymer composite layer to prevent defects.

Efficacy of M3 for the Removal of Toxic Chemicals Such as Chemical Warfare Agents (CWAs)

For the case of CWAs, it anticipated that M3 would be useful as a protective barrier due to the rubbery polymer component and high adsorptive/reactive capacity of the MOFs. Additionally, without wishing to be bound by any particular theory, it is believed that M3 would enable a relatively high MVTR due to the hydrophilicity of the MOFs used within the MMC. Indeed, there was limited permeation (<0.01 mg/$m^3$) of 2-chloroethyl ethyl sulfide (2-CEES), a simulant for the CWA mustard, over 16 h as shown in FIG. 5E (see also FIG. 4 for details). For comparison, 2-CEES instantaneously penetrated laboratory latex gloves of similar thickness leading to permeate concentrations that were an order of magnitude greater than those permeating through M3, as also shown in FIG. 5E.

Figure 6:
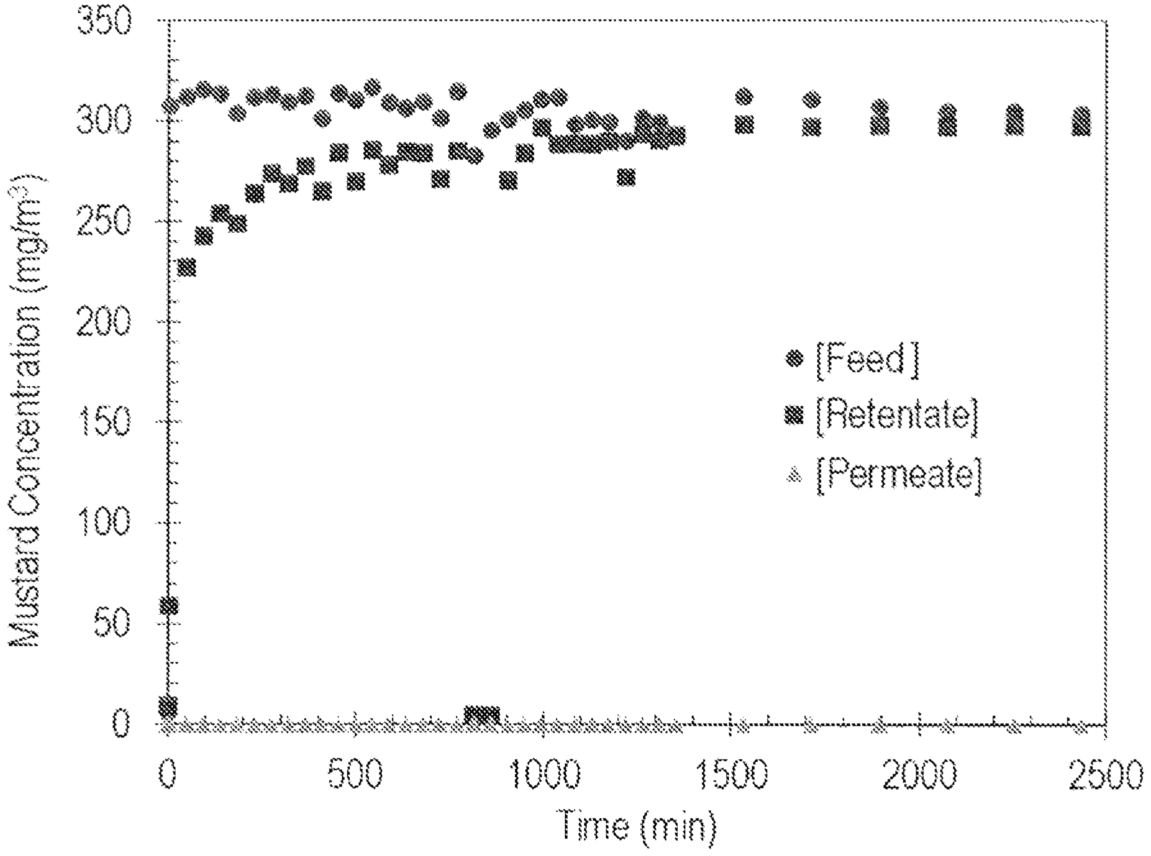
FIG. 6 shows mustard permeation through M3. “Feed” is a constant 300 mg/$m^3$ of mustard. “Retentate” represents the mustard that does not permeate the two-layer structure. “Permeate” is the concentration of mustard that permeates the two-layer structure—in this graph there is almost no measureable mustard that permeates. Note: effluent data points at approximately 800 min are reduced concentration due to a malfunction in the detector; when the malfunction was corrected the data points returned to their ‘pre-malfunction’ trend.
Figure 7:
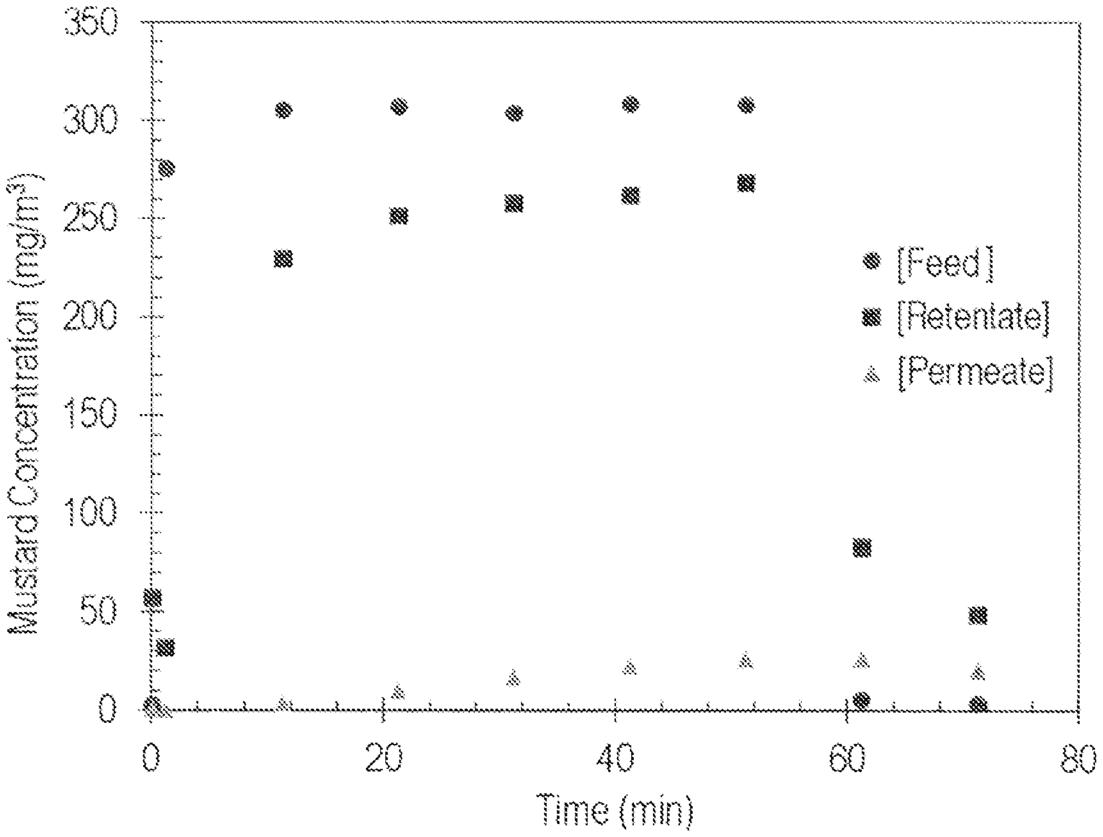
FIG. 7 shows mustard permeation of latex. “Feed” is a constant 300 mg/$m^3$ of mustard. “Retentate” represents the mustard that does not permeate the latex. “Permeate” is the concentration of mustard that permeates the latex.

Next, M3 was challenged with the CWA mustard and M3 exhibited even better barrier properties than against 2-CEES with no breakthrough occurring after 2500 min (>40 h). Permeation data for mustard challenged to M3 and latex are shown in FIGS. 6-7, respectively. Beyond the barrier properties of the multi-layer structure M3 in comparison to latex, the M3 exhibited a MVTR (Table 4) of 16 g/$m^2$/h—an order of magnitude higher than latex.

TABLE 4

MVTR calculations and data.

| Multi-layer structures | Initial jar mass (g) | Final jar mass (g) | Mass lost (g) | Cross-sectional area ($m^2$) | Exposure Time (h) | MVTR (g/$m^2$/h) |
|---|---|---|---|---|---|---|
| M1 | 197.08 | 196.95 | 0.13 | 0.001552 | 24.0 | 3.66 |
| M2 | 197.52 | 197.31 | 0.21 | 0.001552 | 24.0 | 5.61 |
| M3 | 199.82 | 199.23 | 0.58 | 0.001552 | 23.5 | 16.00 |
| M4 | 194.47 | 194.19 | 0.28 | 0.001552 | 24.0 | 7.53 |
| M5 | 198.90 | 198.84 | 0.06 | 0.001552 | 24.5 | 1.66 |
| M6 | 199.08 | 198.98 | 0.01 | 0.001552 | 24.5 | 2.61 |
| M7 | 200.01 | 199.94 | 0.07 | 0.001552 | 24.5 | 1.89 |
| M8 | 199.84 | 199.57 | 0.27 | 0.001552 | 24.0 | 7.28 |
| M9 | 194.77 | 194.69 | 0.08 | 0.001552 | 23.5 | 2.21 |
| Latex | 197.81 | 197.78 | 0.03 | 0.001552 | 22.0 | 1.02 |
| Butyl Rubber | 198.30 | 198.30 | 0.00 | 0.001552 | 20.5 | 0.13 |
| PVDF Nanofiber with 40% MOF | 197.21 | 195.33 | 1.89 | 0.001552 | 20.5 | 59.34 |

These data suggest that not only do these multi-layer structures M-M9 provide enhanced CWA protection in comparison to latex, but they also do so with the ability to provide evaporative cooling, reducing sweat and decreasing the thermal burden to users of potential protective equipment comprised of M3. Although the MVTR value was lower than fiber-based systems, it was significantly higher than current protective barrier equipment. The presence of defects within the film interface actually enhanced these effects, as the CWA had better access to active sites of the MOF, while moisture was more easily transmitted through the composite.

Efficacy of M3 for Separation of Gases

In addition to excellent barrier properties and high MVTR, M3 preferentially adsorbed carbon dioxide ($CO_2$) in comparison to other gases such as methane ($CH_4$), nitrogen ($N_2$), and oxygen ($O_2$), as shown in FIG. 5F. The composite provided an ideal $CO_2$/$N_2$ selectivity of 18.9, a 50% increase over materials made from ZIF-8 and SEBS. Details of the calculations are provided hereinabove.

Figure 8:
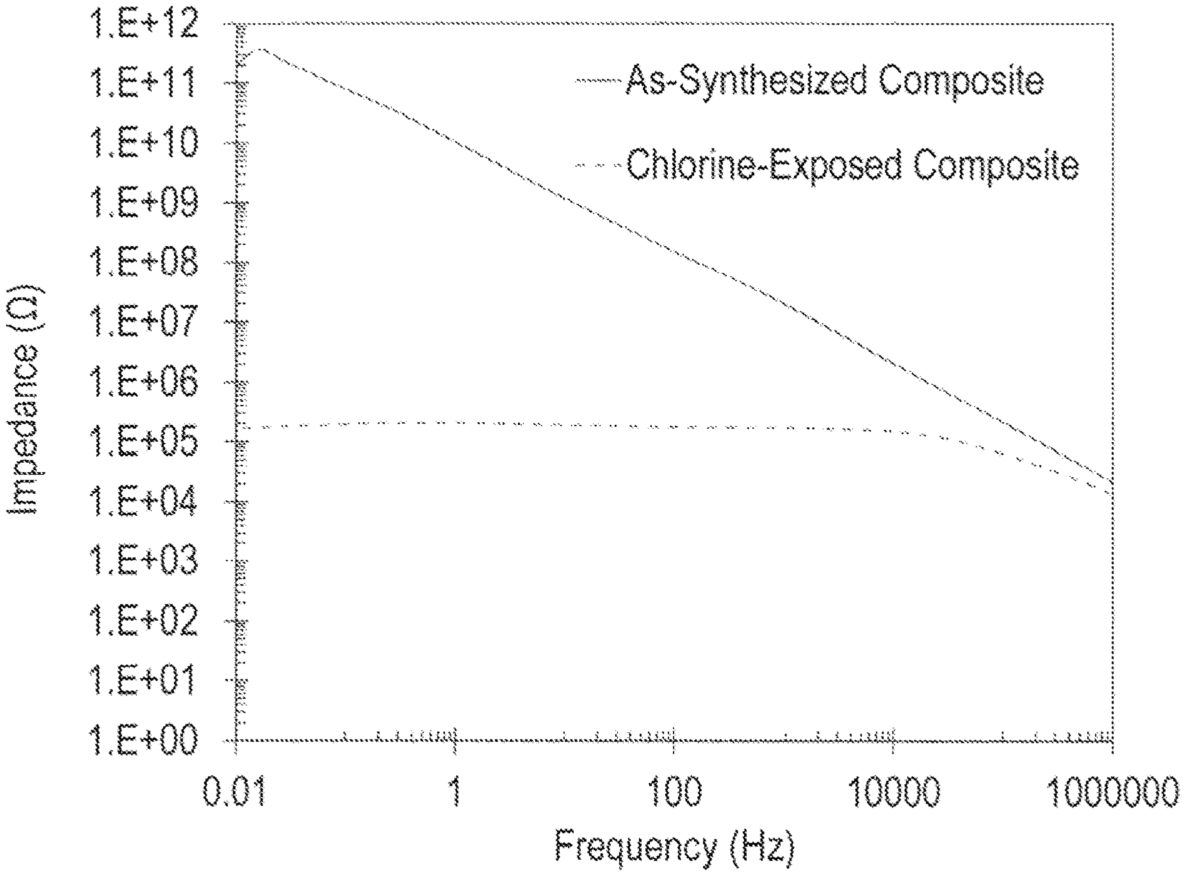
FIG. 8 shows impedance magnitude as a function of frequency for M3 before and after exposure to chlorine gas.

Further enhancements may be realized by optimizing the amount and type of MOF as well as the type of polymer(s) used within each composite layer of the multi-layer structure. The ability of M3 to sense toxic gases also was explored using EIS. FIG. 8 shows that after exposure to chlorine the impedance decreased by six orders of magnitude stemming from the underlying reactivity of UiO-66-$NH_2$ with chlorine.

Bifunctional MOF/Metal Oxide—Multi-Layer Structure, M4

A bifunctional MOF/metal oxide multi-layer structure comprised of UiO-66-$NH_2$ and zirconium hydroxide [$Zr(OH)_4$], M4, for the purpose of a dual-action G-series and V-series nerve agent barrier. UiO-66-$NH_2$ was chosen because of its reactivity towards the G-series nerve agent soman, while $Zr(OH)_4$ is the fastest known solid catalyst for VX detoxification. The MOF and $Zr(OH)_4$ were layered using SEBS at 50 wt % particle loading, using the procedure as described hereinabove.

Efficacy of M4 for the Removal of Toxic Chemical such as CWAs

Figures 9A, 9B:
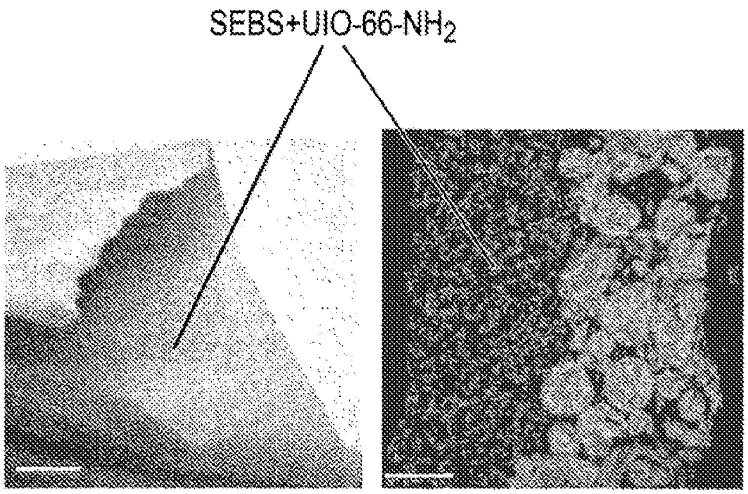
FIGS. 9A and 9B shows (A) Optical and (B) SEM images of the two-layer structure M4 respectively. The composite layer with UiO-66-$NH_2$ is yellow in (A) and the left layer in (B), and the composite layer with $Zr(OH)_4$ is white in (A) and the right layer in (B). Scale bar in (A)=1 cm. Scale bar in (B)=50 μm.
Figure 9C:
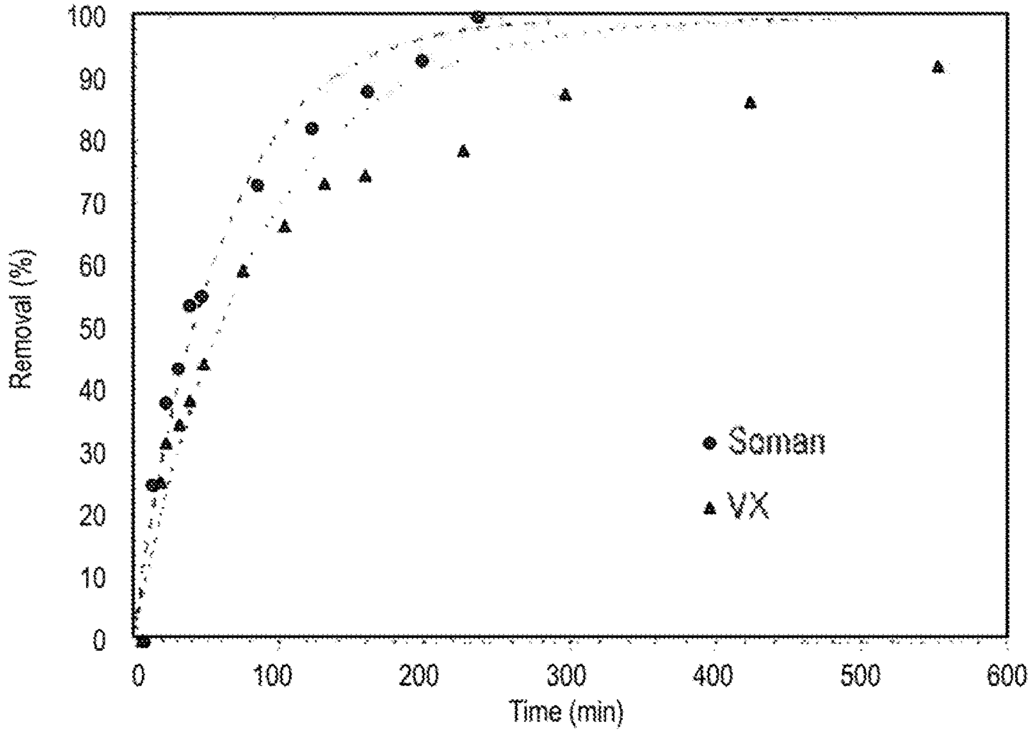
FIG. 9C shows temporal removal data for soman and VX as determined by $^{31}$P MAS NMR by M4. Dotted lines represent first order kinetic models that capture the initial soman and VX degradation behavior.
Figure 13:
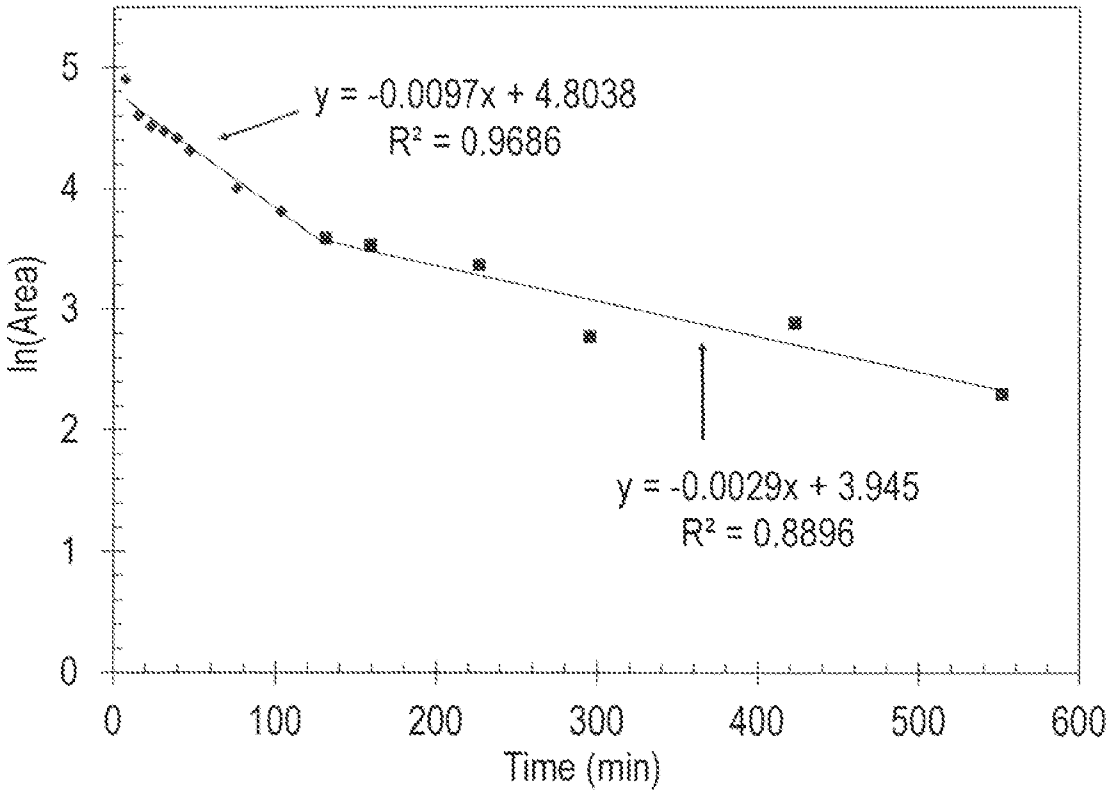
FIG. 13 shows natural log of VX peak area as a function of time for M4 tested using $^{31}P$ MAS NMR. The representative data from FIG. 12 (along with additional time points) were integrated to determine the area under the peaks. The slopes of the curves in this figure were used to calculate half-life of VX exposed to M4.

The efficacy of M4 was evaluated by dropping neat liquid agents onto the composite and measuring degradation rates via $^{31}P$ MAS NMR spectroscopy. NMR data along with optical and SEM images of M4 are shown in FIGS. 9A-9B. The images exhibit clearly delineated layers of both MOF and metal oxide composites within the layered MMC. Both agents reacted on the substrate resulting in the formation of non-toxic products pinacolyl methylphosphonic acid and ethyl methylphosphonic acid for soman and VX, respectively, as determined by NMR (FIGS. 10-13). The calculated rate of disappearance of soman was 54 min while VX disappearance data showed two different regimes, one with a half-life of 71 min and a second one with a half-life of 158 min (FIG. 13). Soman data were well described with a first-order kinetic model with a rate constant of 0.017 $min^{-1}$. VX data initially conformed to first order kinetics with a rate constant of 0.012 $min^{-1}$ and then deviated to a much slower 0.0029 $min^{-1}$. The two regimes for VX removal are consistent with fast initial adsorption into the substrate followed by slower reaction within the pores of the sorbent. It is speculated that faster rates will be achievable through optimization of both polymer and particle loading.

Multi-Layer Structures, M5-M7

Figure 9D:
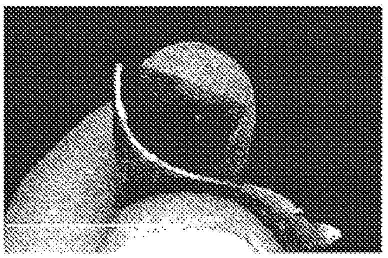
FIGS. 9D-9F shows in (D) that the PMMA-based three-layer structure M7 composite was highly flexible; however, the PMMA layer of M7 broke when stretched (E) but reformed upon release (F). Scale bars in (D)-(F)=1 cm.
Figure 9E:
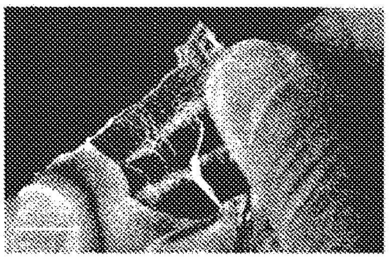
Figure 9F:
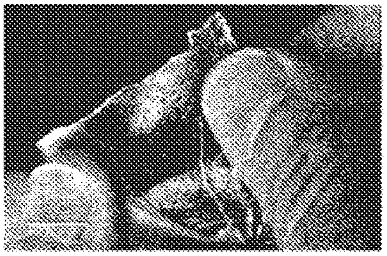
Figure 10:
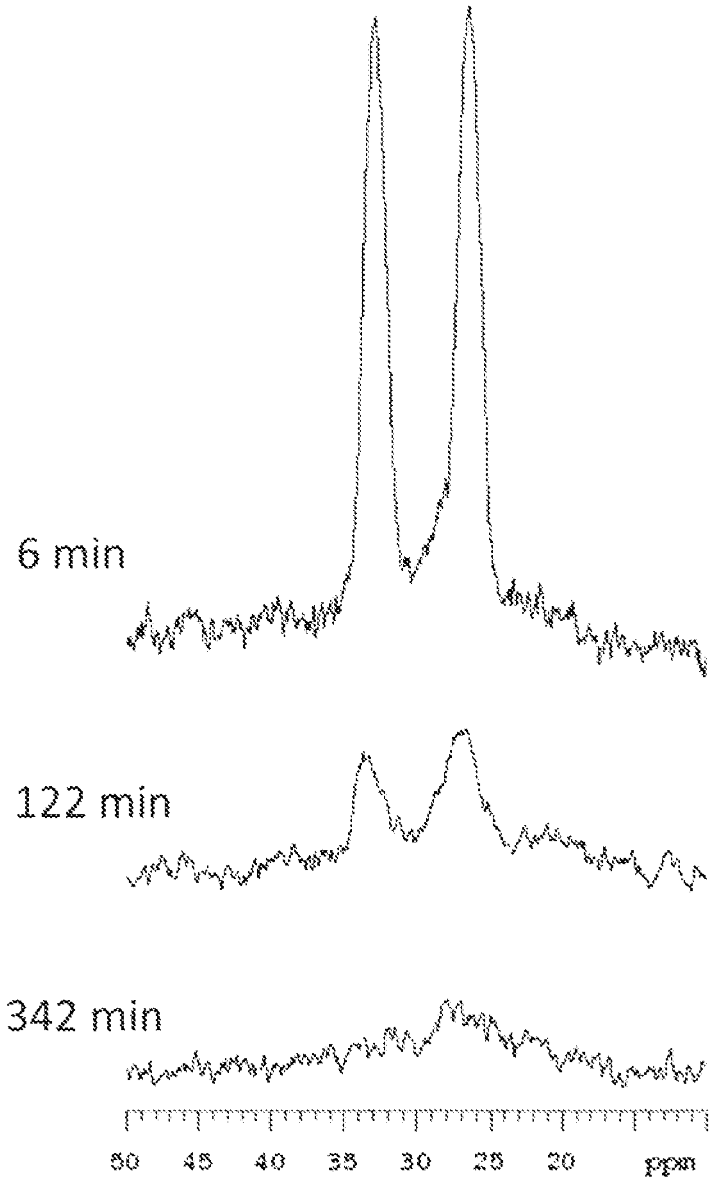
FIG. 10 shows $^{31}$P MAS NMR spectra of soman dosed to M4 as a function of time. As shown, pinacolyl methyl phosphonic acid (PMPA) is generated from the hydrolysis of soman in small quantities but is difficult to discern due to adsorption effects in the substrate. The signature peak for PMPA is the small hump located between 25-30 ppm in the above spectrum at 342 min.
Figure 11:
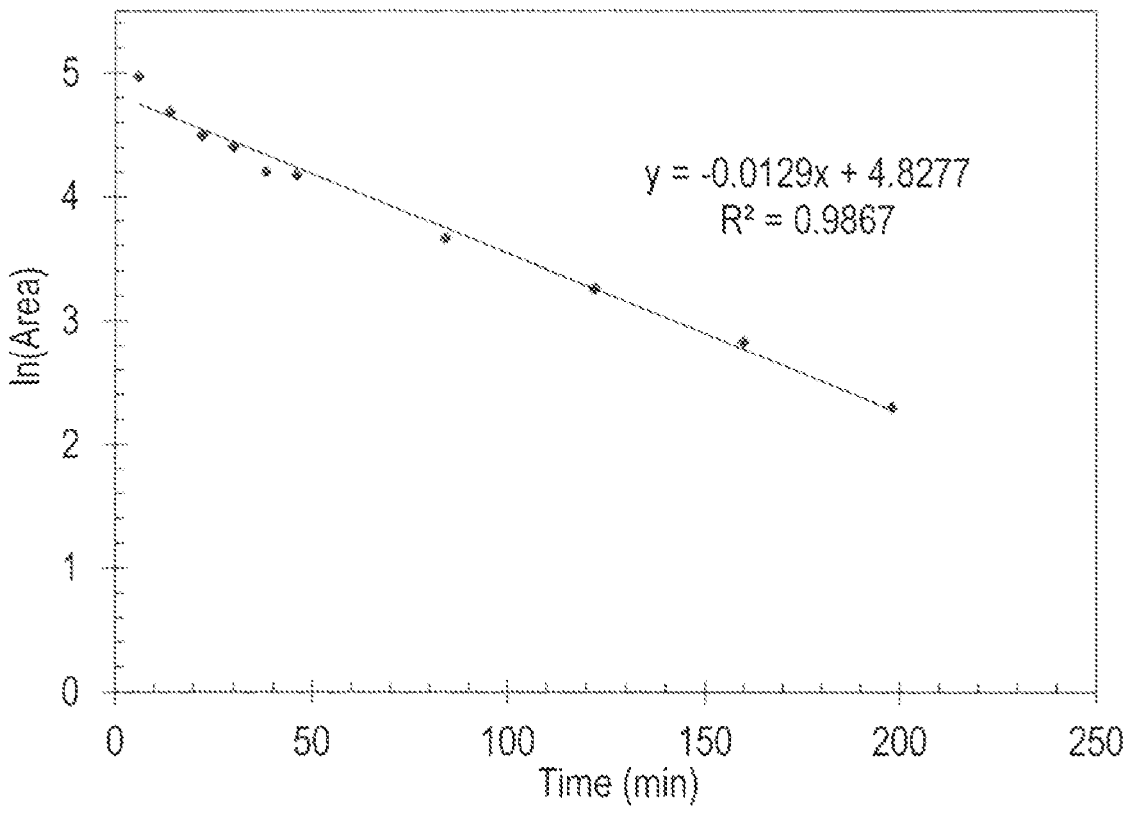
FIG. 11 shows natural log of soman peak area as a function of time for M4 tested using $^{31}P$ MAS NMR. The representative data from FIG. 10 (along with additional time points) were integrated to determine the area under the peaks. The slopes of the curves in this figure were used to calculate half-life of soman exposed to the MMC M4.
Figure 12:
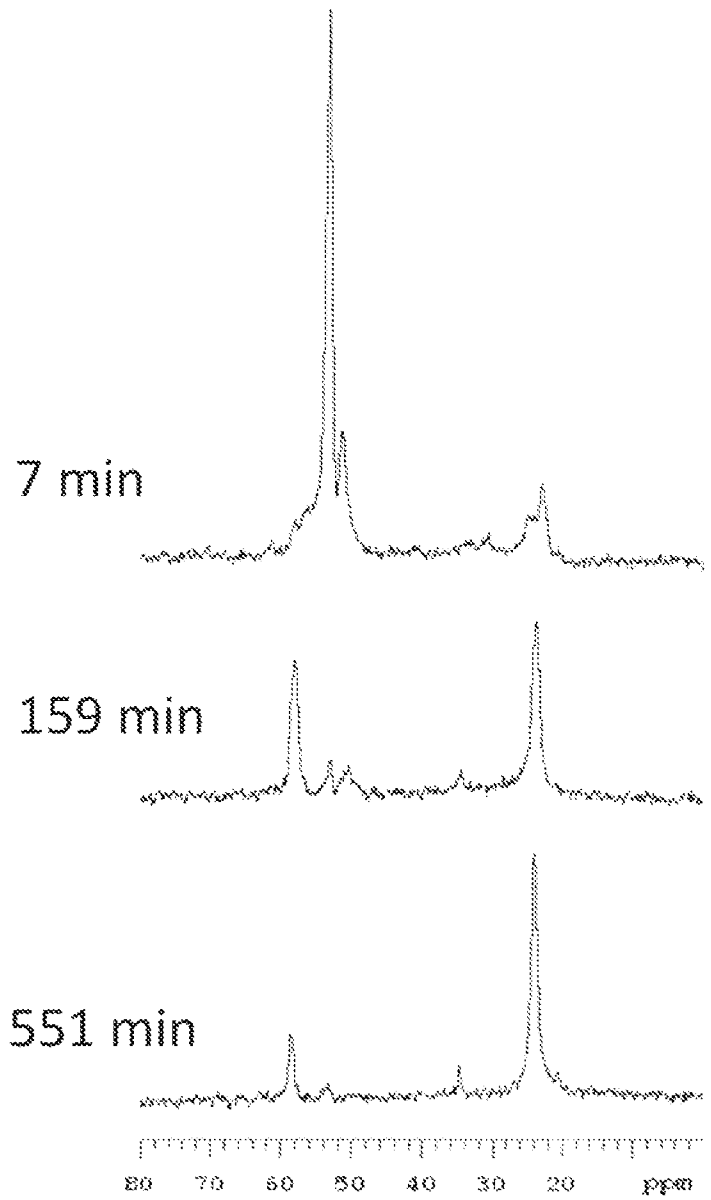
FIG. 12 shows $^{31}P$ MAS NMR spectra of VX (58 ppm) dosed to M4 as a function of time. Ethyl methyl phosphonic acid (EMPA) is generated from the hydrolysis of VX and is present at 24 ppm in the spectra above. Spectra shifted slightly over time due to adsorption onto the substrate.
Figure 14:
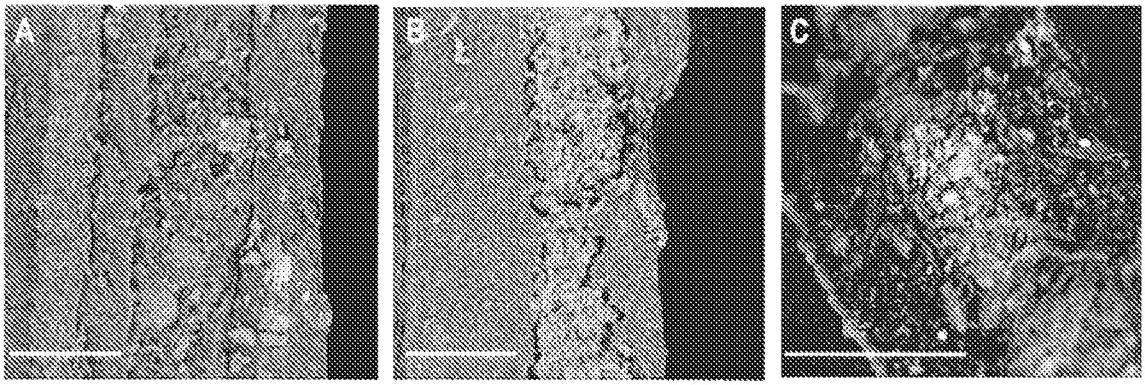
FIG. 14 shows SEM images of the three-layer structures: (A) M5, (B) M6, and (C) M7. Scale bar=50 μm and applies to all images.
Figure 15:
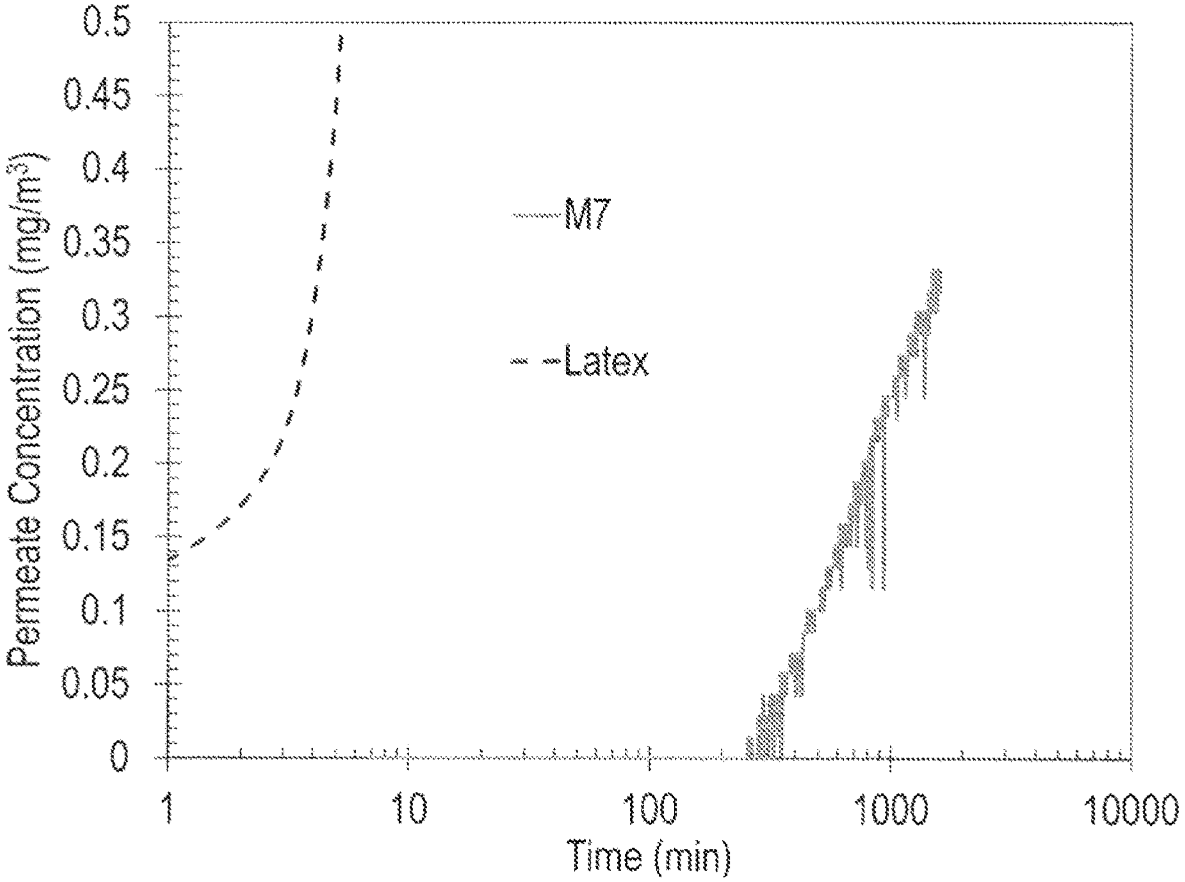
FIG. 15 shows 2-CEES permeation through M7. The multi-layer structure was cracked before testing to determine residual permeation properties. Several hundred minutes of protection exists after cracking the composite. The noise in the M7 data is associated with integration errors due to proximity to the limit of detection.

Additionally, an assortment of polymers as the middle layer with a consistent 67 wt % HKUST-1 loading sandwiched between two SIS layers were constructed. Three resulting multi-layer structures (M5-M7) incorporated PS, PEO, and PMMA, respectively. SEM images of the tri-layer structure of each structure are shown in FIG. 14. These multi-layer structures demonstrated the potential applicability towards hydrophobic/hydrophilic and brittle/flexible layered composites. Of particular interest was M7—the sandwich structure could be folded without catastrophic failure of the inner PMMA active layer. When stretched, it exhibited local breakage; however, it readily reformed back to the original structure as shown in FIGS. 9D-9F. This behavior has important implications for composites and membranes in general but is specifically applicable to CWA protection. Indeed, even after cracking the material provided significant protection against 2-CEES as shown in FIG. 15.

In conclusion, a new strategy for layering MOF/polymer films into hierarchical composites is disclosed hereinabove. The sandwich-like multi-layer structures can be used for a variety of applications through tuning of the polymer, MOF type, MOF wt %, and layer order. Several composites exhibit impact resistant and reactive barrier properties to chemical warfare agents, making these materials applicable for a variety of protection applications. Moreover, the versatility of the multi-layer structures facilitates optimization of composite layers for more demanding applications. This feature is especially apparent with M3 and M4, in which the ability to provide a reactive barrier to CWAs while maintaining high MVTR values has led to the development of a breathable, yet protective, rubber. Further materials engineering for other applications is possible with the incorporation of the appropriate MOF and polymer combinations.

Although the invention is illustrated and described herein with reference to specific embodiments, the invention is not intended to be limited to the details shown. Rather, various modifications may be made in the details within the scope and range of equivalents of the claims and without departing from the invention.

While preferred embodiments of the invention have been shown and described herein, it will be understood that such embodiments are provided by way of example only. Numerous variations, changes and substitutions will occur to those skilled in the art without departing from the spirit of the invention. Accordingly, it is intended that the appended claims cover all such variations as fall within the spirit and scope of the invention.

REFERENCE

1. Lu, A. X.; McEntee, M.; Browe, M. A.; Hall, M. G.; DeCoste, J. B.; Peterson, G. W., MOFabric: Electrospun Nanofiber Mats from PVDF/UiO-66-$NH_2$ for Chemical Protection and Decontamination. *ACS Appl. Mater. Interfaces* 2017, 9 (15), 13632-13636.

What is claimed:

1. A multi-layer structure comprising:

a first composite layer disposed over a second composite layer, wherein the first composite layer comprises 1-99% by weight of a first active material dispersed in a first polymer comprising an elastomeric polymer and the second composite layer comprises 0-99% by weight of a second active material dispersed in a second polymer, wherein the first active material chemically or physically interacts with at least one toxic chemical and is selected from the group consisting of metal-organic frameworks (MOFs), metal oxides, metal hydroxides, zeolites and combinations thereof, wherein the first active material and the second active material are the same as or different from each other, and the first polymer and second polymer are the same as or different from each other, subject to the proviso that the first composite layer and the second composite layer compositionally differ from each other in at least one respect, wherein the elastomeric polymer is an elastomeric block copolymer selected from the group consisting of styrene-based block copolymers, methyl methacrylate-based block copolymers, and olefin-based block copolymers, wherein at least one of the first layer or the second layer comprises a styrene-based block copolymer.

2. The multi-layer structure according to claim 1, wherein the first active material is present in the first composite layer in a concentration which is greater than or equal to the concentration of the second active material in the second composite layer.

3. The multi-layer structure according to claim 1, wherein the first active material is a MOF present in an amount of at least 15% by weight, based on the total weight of the MOF and the first polymer.

4. The multi-layer structure according to claim 1, further comprising a third composite layer, wherein the third composite layer is either disposed over the first composite layer on a side of the multi-layer structure opposite the second composite layer or disposed over the second composite layer on a side of the multi-layer structure opposite the first composite layer, wherein the third composite layer comprises a third active material dispersed in a third polymer, wherein the third polymer is the same as or different from the first polymer or the second polymer, and wherein the third active material is the same as or different from the first active material and the second active material.

5. The multi-layer structure according to claim 4, further comprising one or more additional composite layers, thereby resulting in an n-layer structure, wherein n=4 to 100, wherein at least one of the one or more additional composite layers comprises an active material that is the same as or different from the first active material, the second active material, and/or the third active material.

6. The multi-layer structure according to claim 5, wherein at least one of the second, the third and the one or more additional composite layers comprises an electrospun fiber or composite fiber comprising an MOF dispersed in a polymer.

7. The multi-layer structure according to claim 5, wherein at least one of the first, the second, the third and the one or more additional composite layers comprises a mixture of two or more active materials, and wherein each active material in the mixture of two or more active materials chemically or physically interacts with a different toxic chemical.

8. The multi-layer structure according to claim 7, wherein the mixture of two or more active materials comprises at least one MOF independently selected from the group consisting of zirconium-based MOFs, copper-based MOFs, iron-based MOFs, zinc-based MOFs and mixtures thereof.

9. The multi-layer structure according to claim 1, wherein the first active material is a MOF selected from the group consisting of UiO-66, UiO-66-$NH_2$, UiO-66-X (where X=functional group), UiO-67, ZIF-8, HKUST-1, PCN-250, Cu-MOF-74, and mixtures thereof.

10. The multi-layer structure according to claim 4, wherein the second polymer and the third polymer are independently selected from the group consisting of polyethylene oxide (PEO), polystyrene (PS), poly(methyl methacrylate) (PMMA), poly(vinylidene fluoride) (PVDF), polystyrene-block-isoprene block-styrene (SIS), polystyrene-block-poly(ethylene-ran-butylene)-block-styrene (SEBS), styrene-butadiene rubber (SBR), polystyrene-block-butadiene-block-styrene (SBS), and blends thereof, and wherein the first polymer is selected from the group consisting of SIS, SEBS, SBR, SBS, and blends thereof.

11. The multi-layer structure according to claim 1, wherein the multi-layer structure has a surface area of from 1 to 5,000 $m^2/g$.

12. The multi-layer structure according to claim 5, further comprising one or more adhesive polymeric layers disposed in between and in contact with at least two of the first, the second, the third, and/or the additional composite layers.

13. The multi-layer structure according to claim 5, wherein at least one of the first composite layer, the second composite layer, the third composite layer and/or the additional composite layers further comprises at least one porous material selected from the group consisting of activated carbon, silicas, porous materials, and catalysts.

14. The multi-layer structure according to claim 1, wherein the at least one toxic chemical comprises one or more toxic chemicals selected from the group consisting of ammonia, chlorine, nitrogen dioxide, sulfur dioxide, carbon monoxide, chemical warfare agents, simulants, oils, contaminants, battlefield contaminants, and combinations thereof.

15. The multi-layer structure according to claim 1, wherein the multi-layer structure is a two-layer structure selected from the group consisting of:

(i) 40-60 wt % HKUST-1 in an SEBS block copolymer/40-60 wt % UiO-66-$NH_2$ in an SEBS block copolymer;

(ii) 40-60 wt % UiO-66-$NH_2$ in an SEBS block copolymer/40-60 wt % $Zr(OH)_4$ in an SEBS block copolymer; and (iii) 10-30 wt % UiO-66-$NH_2$ in an SEBS block copolymer/70-90 wt % UiO-66-$NH_2$ in an SEBS block copolymer, wherein the amounts in wt % are based on the total weight of the active material and the polymer in each composite layer.

16. The multi-layer structure according to claim 4, wherein the multi-layer structure is a three-layer structure selected from the group consisting of:

(i) 10-30 wt % UiO-66-$NH_2$ in an SIS block copolymer/50-80 wt % HKUST-1 in an SIS block copolymer/10-30 wt % UiO-66-$NH_2$ in an SIS block copolymer;

(ii) 10-30 wt % HKUST-1 in an SIS block copolymer/50-80 wt % UiO-66-$NH_2$ in an SIS block copolymer/10-30 wt % HKUST-1 in an SIS block copolymer;

(iii) 10-30 wt % UiO-66-$NH_2$ in an SIS block copolymer/50-80 wt % HKUST-1 in polystyrene/10-30 wt % UiO-66-$NH_2$ in an SIS block copolymer;

(iv) 10-30 wt % UiO-66-$NH_2$ in an SIS block copolymer/40-80 wt % HKUST-1 in PEO/10-30 wt % UiO-66-$NH_2$ in an SIS block copolymer;

(v) 10-30 wt % UiO-66-$NH_2$ in an SIS block copolymer/50-80 wt % HKUST-1 in poly(methyl methacrylate)/10-30 wt % UiO-66-$NH_2$ in an SIS block copolymer; and (vi) 10-30 wt % UiO-66-$NH_2$ in an SEBS block copolymer/electrospun 10-30 wt % UiO-66-$NH_2$-PVDF composite fiber/10-30 wt % UiO-66-$NH_2$ in an SEBS block copolymer, wherein the amounts in wt % are based on the total weight of the active material and the polymer in each composite layer.

17. The multi-layer structure according to claim 1, wherein the multi-layer structure is a multi-layer mixed-matrix membrane or a multi-layer mixed-matrix composite.

18. An article comprising a barrier layer against one or more toxic chemicals, the barrier layer comprising the multi-layer structure according to claim 1 as, wherein the article is selected from the group consisting of gloves, boots, clothing, gas masks, tents, filters, and sensors, wherein the one or more toxic chemicals comprise one or more of ammonia, chlorine, nitrogen dioxide, sulfur dioxide, carbon monoxide, chemical warfare agents, simulants, oils, contaminants, battlefield contaminants, and combinations thereof.

19. A process for making the multi-layer structure according to claim 1, comprising:

(i) mixing an active material with a polymer, optionally in an organic solvent, to form a coating composition;

(ii) forming at least one of the composite layers by depositing the coating composition using one or more methods selected from the group consisting of drawn-down coating (doctor blading), spin-coating, dip-coating, spraying, extrusion, casting, and electrospinning;

(iii) repeating steps (i) and (ii) to form an n-layer structure; and (iv) optionally forming an adhesive polymeric layer in between and in contact with two composite layers.

20. A method for removing one or more toxic chemicals comprising the steps of:

(i) providing a multi-layer structure according to claim 1, having an outer surface and an inner surface; and (ii) contacting a feed stream comprising one or more toxic chemicals with the outer surface of the multi-layer structure to produce a toxic chemical-rich retentate stream and a permeate stream, wherein the concentration of one or more toxic chemicals in the permeate stream is less than that present in the retentate stream, wherein the one or more toxic chemicals comprises at least one toxic chemical selected from the group consisting of ammonia, chlorine, nitrogen dioxide, sulfur dioxide, carbon monoxide, chemical warfare agents, simulants, oils, contaminants, battlefield contaminants, and combinations thereof.

21. The method according to claim 20, wherein the multi-layer structure allows transport of moisture vapor through at least one of the one or more composite layers.

22. The method according to claim 20, wherein at least one of the one or more toxic chemicals present in the permeate stream substantially reacts with the active material and/or substantially decomposes before reaching the inner surface of the multi-layer structure.

23. The method according to claim 20, wherein the feed stream comprises atmospheric air, water or a solution.

24. A method for decontaminating a surface contaminated with one or more toxic chemicals, comprising the steps of:

a) contacting a multi-layer structure film according to claim 1 with a contaminated surface;

b) removing the multi-layer structure film from the contaminated surface, thereby resulting in a decontaminated surface;

wherein the decontaminated surface contains a lower amount of one or more toxic chemicals as compared to the contaminated surface.

25. The method of claim 24, wherein the step of contacting a multi-layer structure with a contaminated surface further comprises:

(i) providing a coating composition comprising an active material and a polymer, optionally dispersed in an organic solvent; and (ii) forming a mixed-matric membrane film over the contaminated surface by spraying or drop casting the coating composition over the contaminated surface.

26. The method of claim 24, wherein the step of contacting a multi-layer structure with a contaminated surface further comprises forming a multi-layer structure film by co-extruding a composition comprising an active material and a polymer.

27. A method for sensing one or more toxic chemicals comprising the steps of:

(i) providing a multi-layer structure according to claim 1, having an outer surface and an inner surface;

(ii) contacting a feed stream comprising one or more toxic chemicals with the outer surface of the multi-layer structure to produce a toxic chemical-rich retentate stream and a permeate stream; and (iii) sensing the one or more toxic chemicals in the feed stream by one or more of colorimetric changes, spectral changes, electrical impedance changes, and resistive changes, wherein the one or more toxic chemicals comprise at least one toxic chemical selected from the group consisting of ammonia, chlorine, nitrogen dioxide, sulfur dioxide, carbon monoxide, chemical warfare agents, simulants, oils, contaminants, battlefield contaminants, and combinations thereof.

28. A method for separating gases comprising the steps of:

(i) providing a multi-layer structure of claim 1, having an outer surface and an inner surface; and (ii) contacting a feed stream comprising a mixture of two or more gases, with the outer surface of the multi-layer structure to produce a first gas-rich retentate gas stream and a second gas-rich permeate gas stream, thereby separating the gas mixture into two separate gases.

29. The method of claim 28, wherein the feed stream comprises a mixture of three gases: gas A, gas B, and gas C, wherein the step of contacting the feed stream with the outer surface of the multi-layer structure produces a gases A&B-rich retentate gas stream and a gas C-rich permeate gas stream, and wherein the method further comprises contacting the gases A&B-rich retentate gas stream with the outer surface of another multi-layer structure to produce a gas A-rich retentate gas stream and a gas B-rich permeate gas stream, wherein the feed stream comprises one or more gases selected from the group consisting of oxygen, nitrogen, carbon dioxide and methane.

* * * * *